US006695854B1

(12) United States Patent
Kayan et al.

(10) Patent No.: US 6,695,854 B1
(45) Date of Patent: *Feb. 24, 2004

(54) BLOOD VESSEL CLIP AND APPLICATOR

(75) Inventors: Helmut Kayan, Redwood City, CA (US); James E. Jervis, Atherton, CA (US)

(73) Assignee: General Surgical Innovations, Inc., Norwalk, CT (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/450,921

(22) Filed: Nov. 29, 1999

(51) Int. Cl.[7] .............................................. A61B 17/04
(52) U.S. Cl. ........................ 606/143; 606/157; 606/158
(58) Field of Search ................................. 606/142, 143, 606/157, 158

(56) References Cited

U.S. PATENT DOCUMENTS

| | | | | |
|---|---|---|---|---|
| 3,363,628 A | * | 1/1968 | Wood | 606/142 |
| 4,556,058 A | * | 12/1985 | Green | 606/142 |
| 4,607,638 A | * | 8/1986 | Crainich | 606/219 |
| 4,637,395 A | * | 1/1987 | Casper et al. | 606/143 |
| 4,799,481 A | * | 1/1989 | Transue et al. | 606/142 |
| 4,821,721 A | * | 4/1989 | Chin et al. | 606/143 |
| 4,932,955 A | * | 6/1990 | Merz et al. | 606/142 |
| 4,990,152 A | * | 2/1991 | Yoon | 606/140 |
| 5,015,249 A | * | 5/1991 | Nakao et al. | 606/142 |
| 5,026,379 A | * | 6/1991 | Yoon | 606/141 |
| 5,049,191 A | * | 9/1991 | Nakao et al. | 606/151 |
| 5,192,298 A | * | 3/1993 | Smith et al. | 606/205 |
| 5,645,567 A | * | 7/1997 | Crainich | 606/219 |
| 5,792,149 A | * | 8/1998 | Sherts et al. | 606/142 |
| 5,906,625 A | * | 5/1999 | Bito et al. | 606/142 |
| 6,193,732 B1 | * | 2/2001 | Frantzen et al. | 606/142 |
| 6,226,843 B1 | * | 5/2001 | Crainich | 606/219 |

FOREIGN PATENT DOCUMENTS

| | | | |
|---|---|---|---|
| WO | 9213490 | * | 8/1992 |
| WO | 9952413 | * | 10/1999 |

* cited by examiner

Primary Examiner—Gary Jackson

(57) ABSTRACT

A blood vessel clip applicator preferably includes two twist pins at one end, between which a blood vessel is placed before occlusion. A magazine in the blood vessel clip applicator preferably holds a plurality of blood vessel clips and can be rotated independently from a grip assembly, whereby the twist pins can be rotated to compress a blood vessel held between them. A blood vessel clip is preferably placed on the blood vessel after it has been flattened.

A blood vessel clip preferably comprises spring quality material, and preferably has a head connected to a first leg and a second leg. The magazine preferably has a constricted region adjacent to an exit aperture. As the head enters the constricted region, the compressive force exerted on the head by the constricted region opens the blood vessel clip to an open position.

In an alternate embodiment, a plunger applies a blood vessel clip with a direct stroke. The plunger has a plurality of stepwise indentations used to restrain the blood vessel clips before application and for pushing them all forward substantially simultaneously during application.

In an alternate embodiment, a variety of blood vessel clips having different shapes, cross-sections and grooves are suitable for use with the blood vessel clip applicator. The alternate blood vessel clip preferably have two legs in a "V" configuration and a head connecting the two legs. The constricted region compresses the head of the blood vessel clip as it passes through the constricted region, thereby closing the clip onto the blood vessel. These alternate embodiments may comprise substantially annealed metal.

17 Claims, 15 Drawing Sheets

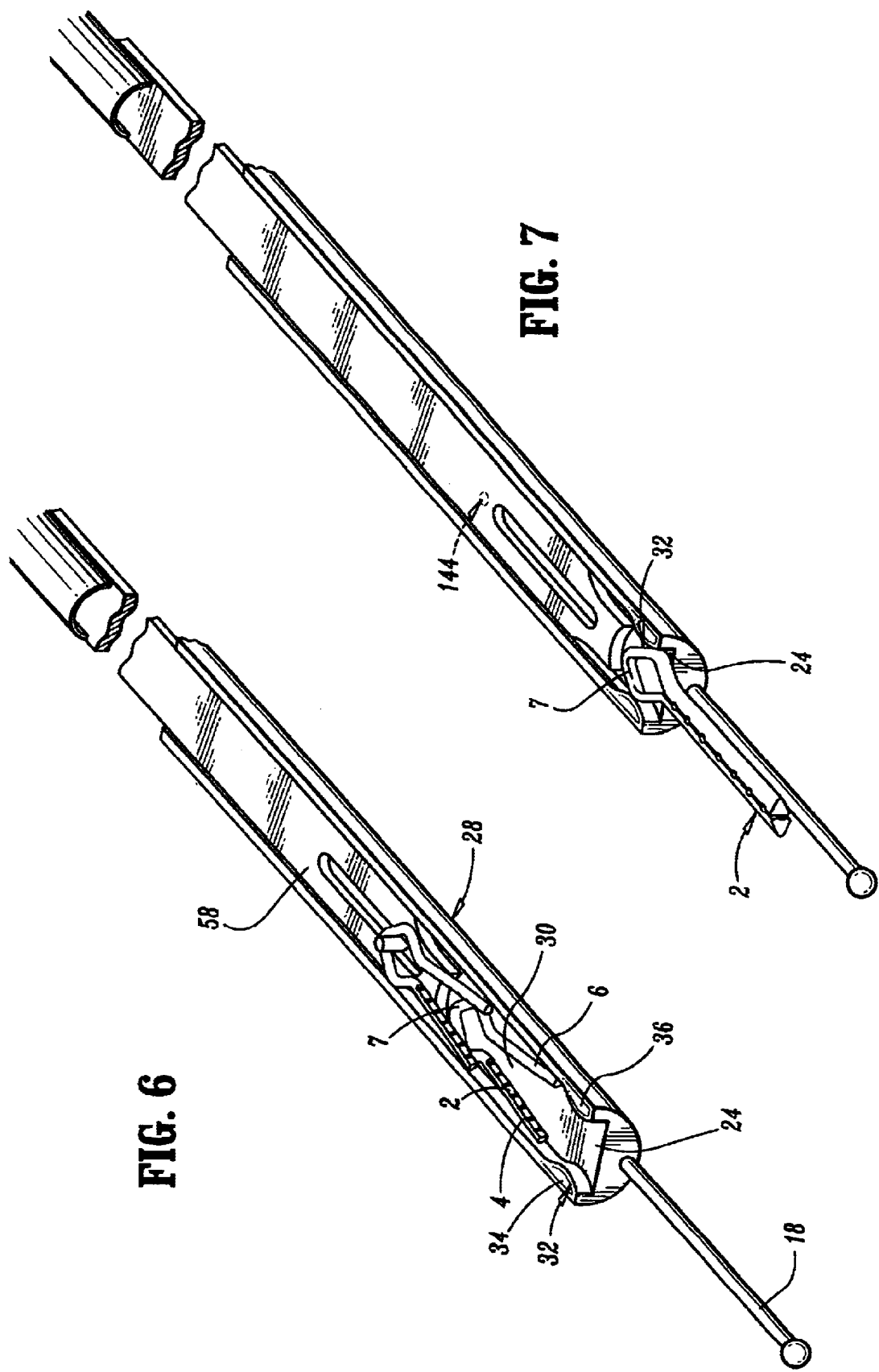

BLOOD VESSEL CLIP AND APPLICATOR

BACKGROUND OF THE INVENTION

The field of invention is minimally invasive vascular surgery, and more specifically an apparatus and method for occluding a blood vessel with clips applied with an applicator extending through a cannula.

Minimally invasive surgery has grown in popularity in the past decade. Minimally invasive surgery (MIS) allows a surgeon to treat a patient while making only tiny incisions in the patient's body, through which surgical devices called cannulae are inserted. A cannula is essentially a thin, hollow tube through which other surgical tools can be inserted into and withdrawn from the patient's body. Because only a small incision is made in the patient's skin for insertion of a cannula, the patient heals faster and experiences less pain than in the aftermath of conventional surgery, in which larger incisions and tools are used.

In several minimally invasive procedures, blood vessels in a patient are permanently occluded. Two common procedures involving blood vessel occlusion are saphenous vein harvest, in which a vein and its branches are occluded so that a portion of that vein can be removed from one location in the body and used in another, and subfascial endoscopic perforator surgery, in which perforator veins are permanently occluded. In recent years, malleable metal clips have been used for permanent occlusion. These clips typically have an opening at one end that is at least as wide as the blood vessel to be occluded. A surgical instrument is inserted through the cannula which places these clips, often serially, in desired locations on blood vessels, then squeezes them shut to achieve permanent occlusion. Such surgical instruments have in the past been bulky enough to require a cannula having an internal diameter of 10 mm or even 12 mm in order to insert them through the cannula to reach the operative site. However, it is often desired to occlude blood vessels having a diameter of 5 mm or less. Ideally, a cannula having an internal diameter of substantially 5 mm would be utilized to occlude a blood vessel having a diameter of 5 mm or less, because the use of a 5 mm cannula is less invasive and traumatic to a patient than a 10 mm or 12 mm cannula. But, as stated above, known surgical instruments for applying blood vessel clips are too large to fit into a cannula having a 5 mm internal diameter, thus requiring the patient to suffer through insertion of a larger-than-optimal cannula for occlusion of blood vessels having a diameter of 5 mm or less.

In addition, malleable blood vessel clips known in the art can rebound after they have been squeezed shut over a blood vessel. Malleability requires that the metal of the clip be in a relatively annealed state, or at least possess adequate elongation to remain intact without cracking or breaking when deformed to achieve closure over the blood vessel. Annealed metal is relatively soft, and this softness is beneficial in that it allows for extreme elongation when substantially annealed metal is shaped into a blood vessel clip. When a malleable clip is closed by a tool, that clip is typically bent in a fashion that causes permanent deformation. Upon removal of the tool, the bent portion of the clip is released. However, the elasticity of the annealed clip can cause it to open slightly upon release of the tool, as the stress in the bend resolves to a net-zero stress condition. Loads placed on the clip, such as the loads exerted by the blood vessel within the clip, serve to increase this rebound. Clip rebound tends to allow opening of the blood vessel, reducing the degree of occlusion. Rebound can thus result in leakage through the vessel, which is undesirable. This rebound increases as the metal in the blood vessel clip is less annealed. Multiple malleable clips may be placed over a single blood vessel to ensure continued occlusion of the blood vessel. However, placement of multiple clips requires additional surgical time and expense.

SUMMARY OF THE INVENTION

In one aspect of a preferred embodiment, a blood vessel clip applicator includes two pins at an end of an applicator barrel distal from a grip assembly, between which two pins a blood vessel is positioned before clip application. In another aspect of a preferred embodiment, the applicator barrel can be rotated independently from the grip assembly, whereby the pins can be rotated to offset and flatten a blood vessel held between them. In another aspect of a preferred embodiment, a blood vessel clip is placed on the blood vessel after the blood vessel has been substantially flattened.

In another aspect of a preferred embodiment, a blood vessel clip comprising a spring-quality material has two legs and a head connecting them, such that the blood vessel clip is biased toward a closed position and openable to an open position. In another aspect of a preferred embodiment, the applicator barrel includes a passage having a constricted region narrower than the head of a blood vessel clip through which the blood vessel clip is forced, thereby opening the blood vessel clip to its open position. The blood vessel clip is placed over the blood vessel through the exit aperture, and applies a constant, known force to the blood vessel after tool removal. In another aspect of a preferred embodiment, a staging space is provided adjacent to the passage having a constricted region for serially loading into it blood vessel clips located in a plane substantially parallel to the plane containing the passage having a constricted region.

In another aspect of a preferred embodiment, a return spring within the grip assembly is attached at one end to the ratchet rod to retract the ratchet rod at the end of its stroke, and at its other end to a revolving member which prevents the return spring from twisting or kinking during rotation of the applicator barrel.

In an alternate embodiment, a plunger applies a blood vessel clip with a direct stroke. In an aspect of the alternate embodiment, a spring or springs bias the plunger downward to contact a plurality of blood vessel clips. In another aspect of the alternate embodiment, the plunger has a plurality of stepwise indentations used to restrain the blood vessel clips before application and for pushing them all forward substantially simultaneously during application. In another aspect of the alternate embodiment, a lock mechanism is attached to a magazine passage containing the blood vessel clips; the lock mechanism includes a plurality of spring tabs adapted to prevent substantial rearward motion of the blood vessel clips within the magazine passage.

In alternate embodiments, a variety of malleable blood vessel clips having different shapes, cross-sections and grooves are suitable for use with the blood vessel clip applicator. In such alternate embodiments, the blood vessel clip typically has two legs in a "V" configuration and a head connecting the two legs. In another aspect of an alternate embodiment, the passage having a constricted region in said applicator barrel compresses the head of the alternate blood vessel clip as the blood vessel clip is forced through the constricted region, thereby closing the clip onto the blood vessel.

Other and further objects and advantages will appear hereinafter.

BRIEF DESCRIPTION OF DRAWINGS

FIG. 6 is a perspective view of a portion of a clip magazine before application of a blood vessel clip.

FIG. 7 is a perspective view of a portion of a magazine after applying a blood vessel clip.

DETAILED DESCRIPTION OF THE PREFERRED EMBODIMENTS

Figure 1:
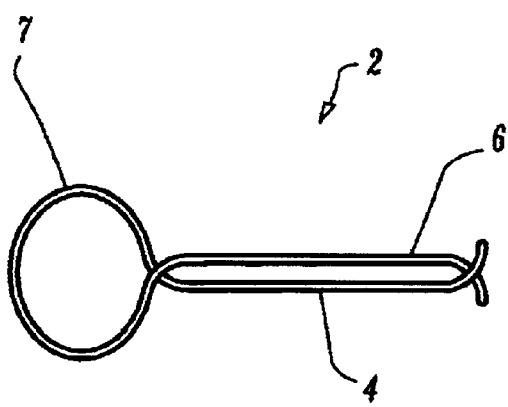
FIG. 1 is a top view of a preferred embodiment of a blood vessel clip.
Figure 2:
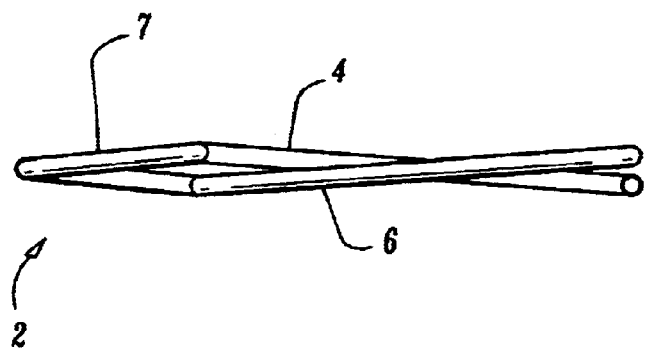
FIG. 2 is a side view of a preferred embodiment of a blood vessel clip in a closed position.

Referring to FIG. 1, a preferred embodiment of a blood vessel clip 2 can be seen. A first leg 4 and a second leg 6 are connected by a head 7. In a preferred embodiment, the head 7 is substantially circular. A top view of the preferred blood vessel clip 2 can be seen in FIG. 1, and a side view of the blood vessel clip 2 can be seen in FIG. 2. As can be seen, the first leg 4 crosses over the second leg 6. However, it is equally effective to manufacture the blood vessel clip 2 such that the first leg 4 crosses under the second leg 6. In a preferred embodiment, the proximal end of the first leg 4 is located substantially above the proximal end of the second leg 6, and the distal end of the first leg 4 is located substantially below the distal end of the second leg 6. By arranging the first leg 4 and the second leg 6 in this manner, the lateral stability of the blood vessel clip 2 is increased.

Figure 3:
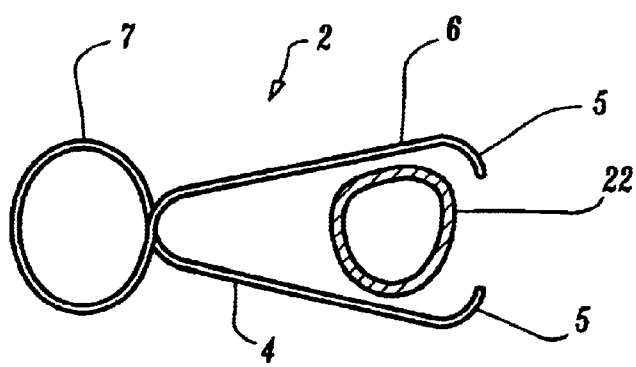
FIG. 3 is a side view of a preferred embodiment of a blood vessel clip in a open position.

In a preferred embodiment, the blood vessel clip 2 comprises a spring-quality material, such as stainless steel or titanium. Other spring-quality materials may be used, and are within the scope of the preferred embodiment. The blood vessel clip 2 has a closed position, as shown in FIG. 1, and an open position, as shown in FIG. 3. The blood vessel clip 2 is constructed such that in the absence of external forces, it assumes the closed position shown in FIG. 2. Due to the spring-quality material comprising the blood vessel clip 2, the blood vessel clip will attempt to return to the closed position after it has been opened to the open position. As can be seen in FIG. 3, and as will be described in greater detail below, the blood vessel clip 2 in the open position is placed over a blood vessel 22. Two curled members 5 face substantially toward one another in the open position, and assist in holding the blood vessel clip 2 on the blood vessel 22. The blood vessel clip 2 is applied to a blood vessel 22 with a clip applicator 50. In a preferred embodiment, a curled member 5 extends from the distal end of both the first leg 4 and the second leg 6, as seen in FIG. 3. The curled members 5 extend in generally the same plane as the blood vessel clip 2, and are oriented such that when the blood vessel clip 2 is in the open position the curled members 5 point into the space between the first leg 4 and the second leg 6. By pointing into any space that may exist between the first leg 4 and the second leg 6 after application onto a blood vessel 22, the curled members 5 assist in preventing the blood vessel 22 from escaping the blood vessel clip 2 through its distal end.

Figure 4:
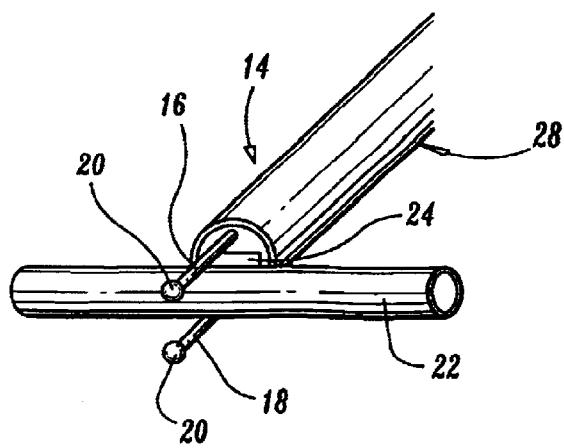
FIG. 4 is a perspective view of the distal end of a clip applicator being placed over a blood vessel.

Turning to FIG. 4, the distal end 14 of the clip applicator 50 can be seen. The distal end 14 is located at one end of a magazine 28 attached to an applicator barrel 54. The applicator barrel 54 is preferably a hollow tube, inside which several components of the clip applicator 50 are located. A first pin 16 and a second pin 18 are preferably spaced apart at substantially 180 degrees from one another, and extend outward from the distal end 14, preferably substantially parallel to the centerline of the magazine 28 and to one another. The first pin 16 and the second pin 18 may optionally be attached directly to the applicator barrel 54. The first pin 16 and the second pin 18 preferably have smooth, atraumatic surfaces. In a preferred embodiment, a ball 20 is attached to the distal end of the first pin 16. Similarly, another ball 20 is preferably attached to the distal end of the second pin 18. An exit aperture 24 can also be seen in the distal end 14 of the clip applicator 50. The exit aperture 24 is located between the first pin 16 and the second pin 18. In a preferred embodiment, the exit aperture 24 is substantially perpendicular to a line extending between the first pin 16 and the second pin 18. However, the exit aperture 24 may form a different angle with a line extending between the first pin 16 and the second pin 18, so long as a blood vessel clip 2 exiting the exit aperture 24 moves into place over a blood vessel 22. The operation of the clip applicator to apply a blood vessel clip 2 to a blood vessel 22 will be described in detail further below.

Figure 8:
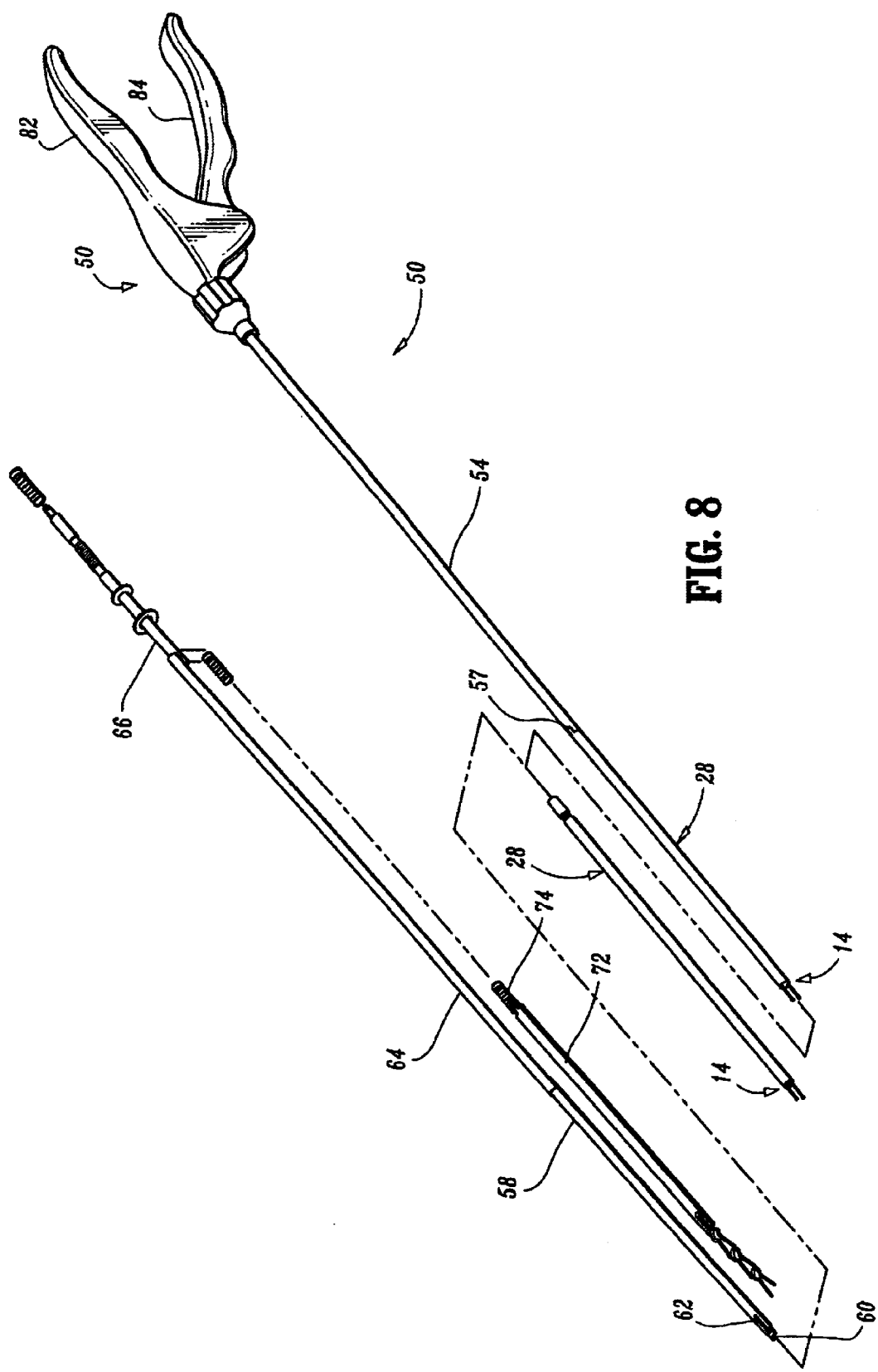
FIG. 8 is an exploded view of the clip applicator.

The blood vessel clip 2 can be applied to the blood vessel 22 through the exit aperture 24 with a variety of mechanisms. Referring to FIG. 8, in a preferred embodiment, a clip applicator 50 is shown in an exploded view. The distal end 14 described above can be seen clearly in relationship to the overall clip applicator 50. As disclosed above, the distal end 14 is located at one end of a magazine 28. The magazine 28, as will be described more fully below, contains the magazine passage 30 and one or more blood vessel clips 2 therein for use in a patient. The magazine 28 also includes a passage having a constricted region 32 adjacent to the exit aperture 24.

As shown in the exploded view in FIG. 8, a plunger 58 is located within the magazine 28. The plunger 58 has a plunger tip 60 that is adapted to push blood vessel clips 2 out of the magazine 28, the plunger tip 60 being shaped such as to extend into the passage having a constricted region 32 an adequate distance to push the blood vessel clip 2 through the exit aperture 24. In a preferred embodiment, the plunger 58 has a plunger slot 62 extending through the plunger 58 near the plunger tip 60. The plunger slot 62 is preferably longer in the direction along the centerline of the magazine 28. In a preferred embodiment, the plunger 58 is attached to a connecting piece 64. The connecting piece 64 is preferably a half-round piece; that is, a thin-walled open-ended half cylinder. The connecting piece 64 is connected to a ratchet rod 66 at its proximal end. The plunger 58, the connecting piece 64 and the ratchet rod 66 are sized and shaped to fit within the applicator barrel 54.

Figure 9:
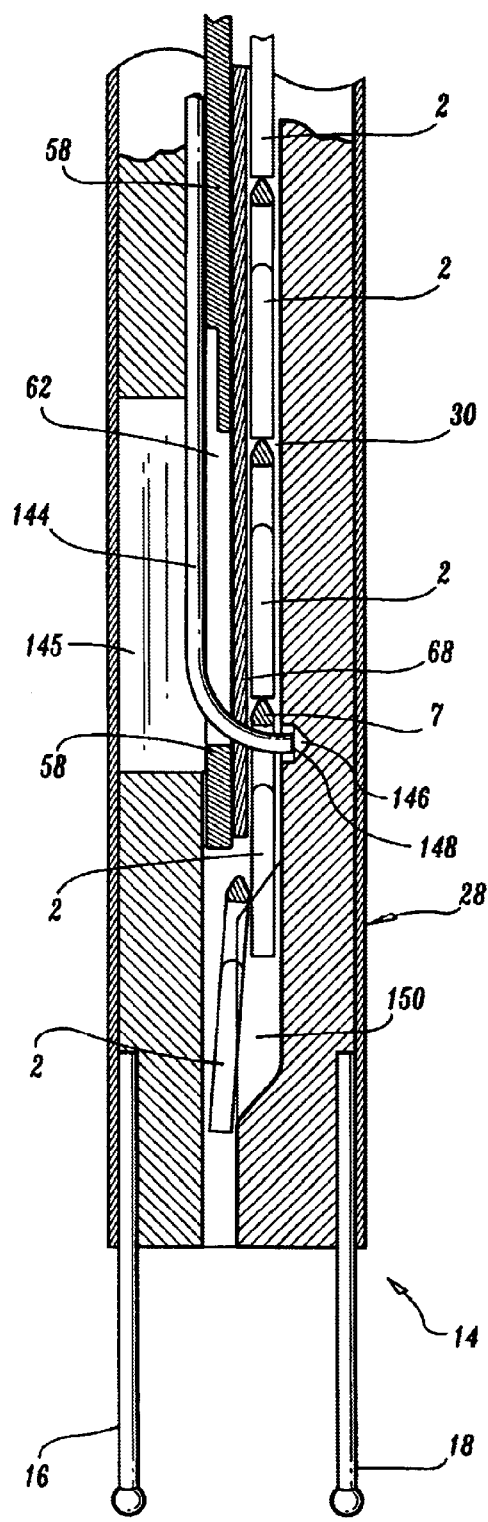
FIG. 9 is a cross-section view of the magazine.

Referring to FIG. 9, a divider shim 68 can be seen within the magazine 28. The plunger 58 occupies a plunger space 70 on one side of the divider shim 68. The magazine passage 30 is located on the opposite side of the divider shim 68. A plurality of blood vessel clips 2 are located within the magazine passage 30. This plurality of blood vessel clips 2 may be referred to as the clip stack. Referring back to FIG. 8, the plurality of blood vessel clips 2 within the magazine passage 30 can also be seen in the exploded view. A clip pusher 72 also occupies a space within the magazine passage 30, located proximal to the plurality of blood vessel clips 2. The clip pusher 72 is attached at its proximal end to a compression spring 74. In a preferred embodiment, the compression spring 74 fits within the connecting piece 64, which is shaped as a half-round piece. The connecting piece 64 preferably transmits force to the distal end 14 without interfering with the compression spring 74. The proximal end of the compression spring 74 is attached to the ratchet rod 66. The compression spring 74 applies a substantially constant force to the plurality of blood vessel clips 2 located in the magazine passage 30, pushing them toward the distal end 14 of the magazine 28. When the magazine 28 is changed, as when the magazine 28 has exhausted its supply of blood vessel clips 2, the magazine 28 is removed from the applicator barrel 54. The plunger 58 slides out of the magazine 28. When the new magazine 28 is attached to the applicator barrel 54, the plunger 58 is slid into the plunger space 70 of the new magazine 28. When the plunger slot 62 engages a clip stack stop spring 144, which is described in greater detail below, the plunger 58 is properly seated in the magazine 28, and use of the clip applicator 50 can continue.

Figure 13:
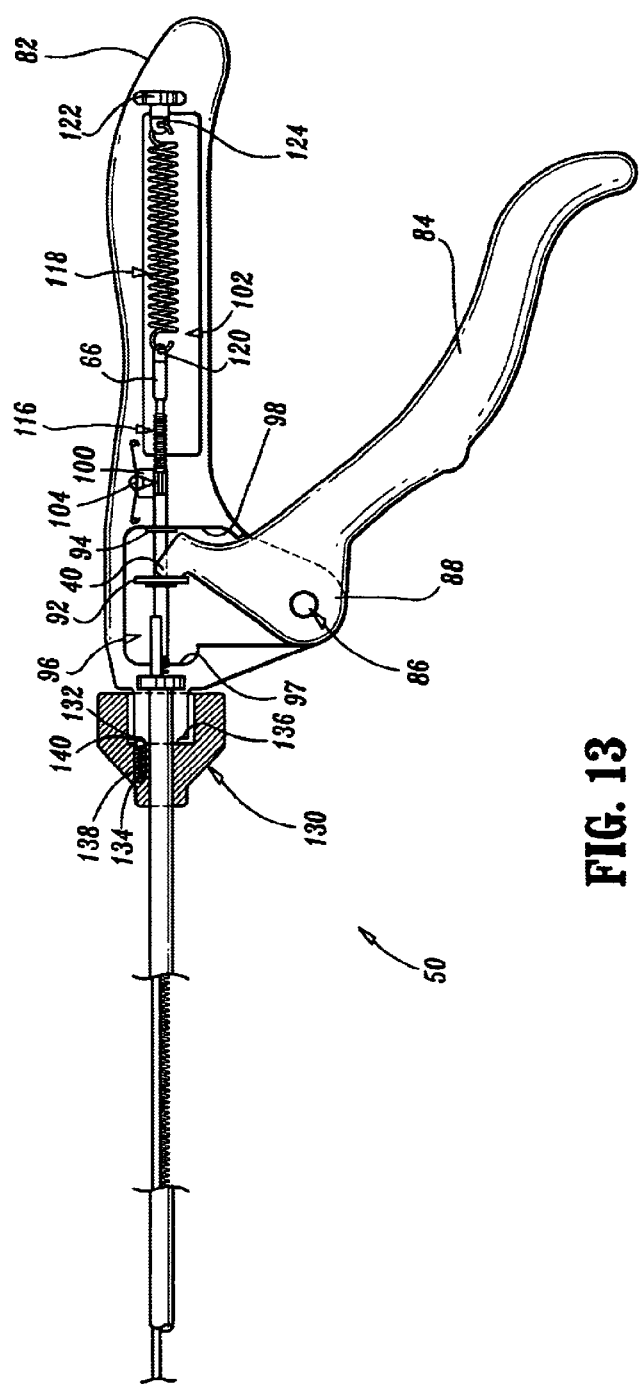
FIG. 13 is a cross-section view of the clip applicator.

Referring to FIG. 13, the ratchet rod 66 extends into a grip assembly 80. The grip assembly 80 includes a handle 82 and a trigger 84. The handle 82 and the trigger 84 can be seen in outline view. The contents of the grip assembly may generally be seen in FIGS. 6, 8 and 9. The trigger 84 moves in an arcuate manner around a pivot 86 when the trigger 84 is squeezed toward the handle 82. A trigger lever 88 is attached to the trigger 84, preferably extending toward the handle 82. The trigger lever 88 has an actuation end 90. The trigger lever 88 is oriented relative to the trigger 84 such that when the trigger 84 is squeezed, the actuation end 90 moves in an arcuate manner as well and encounters an actuation plate 92 attached to the ratchet rod 66. In a preferred embodiment, the actuation plate 92 is substantially circular and substantially coaxial with the ratchet rod 66. The motion of the trigger lever 88 is such that the actuation end 90 has a significant component of motion in a substantially forward direction, that is, toward the distal end 14. When the actuation end 90 encounters the actuation plate 92, the ratchet rod 66 is urged toward the distal end 14. The trigger lever 88 and the actuation plate 92, among other components, extend into a handle chamber 96 having a front wall 97 and a rear wall 98. The actuation plate 92 moves forward until it encounters the front wall 97. The placement of the actuation plate 92 on the ratchet rod 66 thus determines the stroke length of the ratchet rod, because the ratchet rod 66 cannot proceed further after the actuation plate 92 encounters the front wall 97. It should be noted here that the direction along the ratchet rod 66 has been and will be referred to as the longitudinal dimension; the forward direction is the direction toward the distal end 14 of the clip applicator 50 and the backward or rearward direction is the direction away from the distal end 14 along the longitudinal dimension.

In a preferred embodiment, the ratchet rod 66 extends through the rear wall 98, through a pawl chamber 100, and into a rear chamber 102. The ratchet rod 66 is preferably attached at one end to a return spring 118, which is preferably located in the rear chamber 102. The return spring 118 may be attached to the ratchet rod 66 by any reliable means of attachment. Preferably, one end of the return spring 118 is simply inserted into a hole 120 extending through one end of the ratchet rod 66. The other end of the return spring 118 is preferably attached to a revolving member 122 within the handle 82, by simply inserting one end of the return spring 118 into a hole 124 in the revolving member 122. The revolving member 122 is substantially free to rotate around an axis substantially coaxial with the ratchet rod 66. The revolving member 122 prevents the return spring 118 from kinking during operation of the clip applicator 50, by rotating in place to substantially relieve torsional stresses on the return spring 118 caused by rotation of the ratchet rod 66.

When the trigger 84 is released, the actuation end 90 of the trigger lever 88 is pulled backward by the return spring 118. A retraction plate 94 is attached to the ratchet rod 66. As with the preferred actuation plate 92, the retraction plate 94 is preferably substantially circular and substantially coaxial with the ratchet rod 66. As the ratchet rod 66 moves backward under the force of the return spring 118, the retraction plate 94 encounters the rear wall 98 and prevents further rearward motion of the ratchet rod 66. In a preferred embodiment, the retraction plate 94 is attached to the ratchet rod 66 in a location on the ratchet rod 66 such that the compression spring 74 retains some tension even when the retraction plate 94 is at rest against the rear wall 98. By maintaining tension in the compression spring 74, a constant longitudinal force is exerted against the blood vessel clips 2 in the magazine 28.

In a preferred embodiment, the pawl chamber 100 includes a pawl 104 extending thereinto. The pawl 104 has a pawl tip 106 extending into the pawl chamber 100 such that the pawl tip 106 is capable of engagement with the ratchet rod 66. The pawl 104 also contains a pawl passage 108 through which a pawl spring 110 extends. The pawl spring 110 is preferably a leaf spring. The pawl spring 110 is held in place by a first post 112 and a second post 114 within the handle 82. The pawl 104 is mounted in the pawl chamber 100 in such a way that it can swivel backward and forward along an axis substantially perpendicular to the ratchet rod 66. The ratchet rod 66 preferably has a plurality of annular grooves 116. The annular grooves 116 are located on the ratchet rod 66 in such a way as to engage the pawl 104 at certain times during operation of the clip applicator 50. As the ratchet rod 66 moves forward, the pawl tip 106 encounters the annular grooves 116, and swivels forward. The annular grooves 116 prevent the ratchet rod 66 from sliding backward before completion of its forward motion. If the ratchet rod 66 were to attempt to move backward, it would be prevented from doing so by the pawl tip 106, pointed forward and wedged into one of the annular grooves 116. However, when the ratchet rod 66 completes its forward motion, the annular grooves 116 move forward past the pawl 104, freeing it. The pawl spring 110 then pushes the pawl 104 back to a neutral position. During the return motion of the ratchet rod 66 in a backward direction, the pawl 104 swivels backward and the pawl tip 106 once again engages the annular grooves 116. The pawl 104 prevents the ratchet rod 66 from moving forward before its backward motion is complete, in the same manner that the pawl 104 ensures a complete stroke in the forward direction.

As can be seen in FIG. 13, a rotating knob 130 is attached to the ratchet rod 66. When the rotating knob 130 is turned, the applicator barrel 54 is rotated around its axis. In a preferred embodiment, the applicator barrel 54 runs through substantially the center of the rotating knob 130 such that the two are substantially coaxial. However, it will be known to one skilled in the art that a variety of gears or other means could be used to place the rotating knob 130 in a different orientation or location on the clip applicator 50, and still achieve the result of rotating the attachment barrel 54 substantially about its axis when the rotating knob 130 is turned. When the attachment barrel 54 is rotated about its axis, the magazine 28 attached to the attachment barrel 54 rotates as well, and the distal end 14 rotates with the magazine 28. It will be seen that the rotation of the attachment barrel 54 tends to impart rotation to the ratchet rod 66 as well, due to friction between the attachment barrel 54 and the ratchet rod 66. If the ratchet rod 66 rotates, that rotation also imparts torsion to the return spring 118 within the rear chamber 102. The revolving member 122 allows the return spring 118 to rotate if the ratchet rod 66 rotates, and prevents the return spring 118 from becoming twisted. When the blood vessel 22 has been positioned between the first pin 16 and the second pin 18, the rotating knob 130 is turned in order to flatten the blood vessel 22, as previously described. In a preferred embodiment, an indexing ball 132, an indexing spring 134, and one or more index marks 136 are provided to assist the user in controlling rotation of the attachment barrel 54. The indexing spring 134 is located within an index cavity 138 within the rotating knob 130, the index cavity 138 being oriented substantially parallel to the attachment barrel 54. The indexing ball 132 is also located within the index cavity 138. The index cavity 138 preferably opens out to the rear of the rotating knob 130, and possesses a diameter at its opening 140 to the outside less than the diameter of the indexing ball 132. The indexing ball 132 is held against the opening 140 by the indexing spring 134. The handle 82 preferably extends up to the opening 140 in the rotating knob 130. In a preferred embodiment, the index mark or marks 136 are preferably half-spherical depressions in the handle 82 having a diameter substantially the same as the indexing ball 132, spaced substantially sixty degrees apart from one another. However, larger or smaller angular increments may be used if desired. When the indexing ball 132 encounters one of the index marks 136, the indexing spring 134 pushes it into that index mark 136, giving the user an indication that the rotation knob 130 has been rotated successively in an increment, and providing some resistance against further rotation of the rotating knob 130. Of course, other methods of indexing will be known to one skilled in the art, and may be utilized here if desired. For example, a preferred initial position can be defined for the rotating knob 130, and the rotating knob 130 could be biased toward that position. In this alternate embodiment, a single index mark 136 could be used, located at a preferred angle from the preferred initial position of the rotating knob.

While manual operation of the rotating knob 130 has been disclosed above, it will be appreciated that it is within the capability of one of ordinary skill in the art to add a motor and control devices in order to rotate the rotating knob 130.

The operation of the clip applicator 50 will now be described further. Many of the details of this process have been disclosed in greater detail above. The clip applicator 50 is inserted into a patient by sliding the applicator barrel 54 through a cannula (not shown), distal end 14 first. As described above, the distal end 14 is positioned over a blood vessel 22 such that the blood vessel 22 lies between the first pin 16 and the second pin 18. After the user confirms that the blood vessel 22 is thus properly in place, the user rotates the rotating knob 130, thereby rotating the distal end 14 as well. As described above, the portion 26 of the blood vessel 22 between the first pin 16 and the second pin 18 stretches and flattens. The exit aperture 24 is then substantially perpendicular to the plane defined by the flattened portion 26 of the blood vessel 22. The blood vessel 22 is then in position for application of a blood vessel clip 2. It will be appreciated that the distal end 14 need only be rotated so far as to flatten the portion 26 of the blood vessel 22 caught between the first pin 16 and the second pin 18 enough to allow application of the blood vessel clip 22 over that portion 26 of the blood vessel 22. That is, the distal end 14 need only be rotated enough to substantially close the blood vessel 22. As an example, more rotation will generally be required to flatten a blood vessel 22 having a diameter substantially equal to the distance between the first pin 16 and the second pin 18 than is required to position a clip over a blood vessel 22 having a smaller diameter.

To apply a blood vessel clip 2, the user of the clip applicator 50 squeezes the trigger 84 toward the handle 82. The actuation end 90 of the trigger lever 88 pushes the actuator plate 92 forward until the actuator plate 92 touches the front wall 97, allowing for a constant and predictable stroke length. As the actuator plate 92 moves forward, the ratchet rod 66 is urged forward as well. As the ratchet rod 66 moves forward, the connecting piece 64 attached to it moves forward as well, as does the plunger 58 connected to the connecting piece 64.

Figure 12:
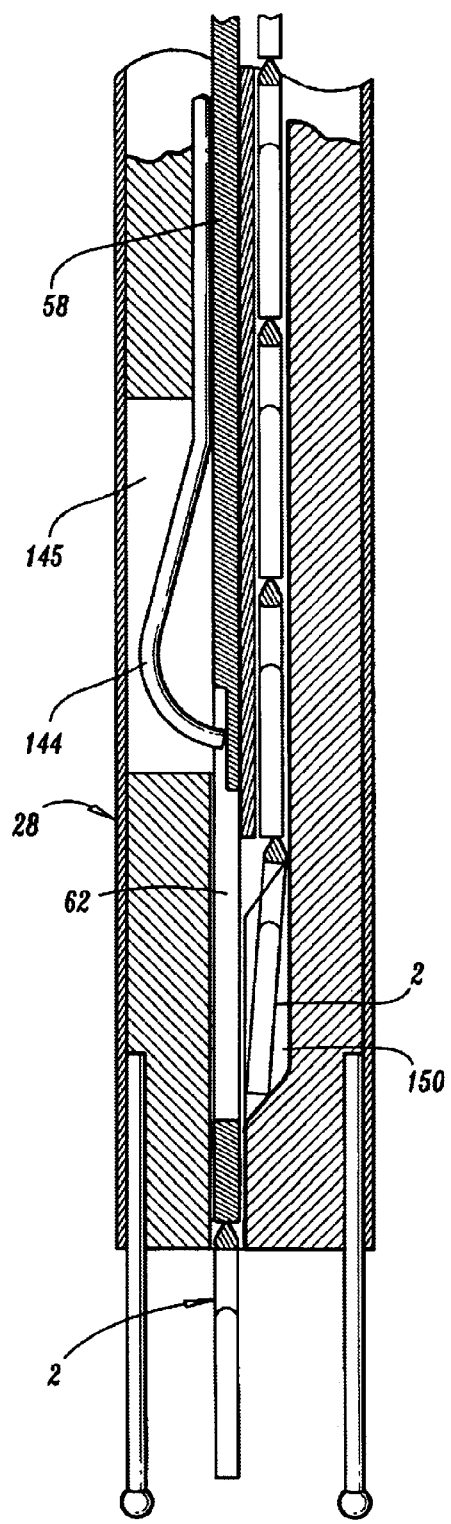
FIG. 12 is a cross-section view of the magazine, as a blood vessel clip is ejected.
Figure 14:
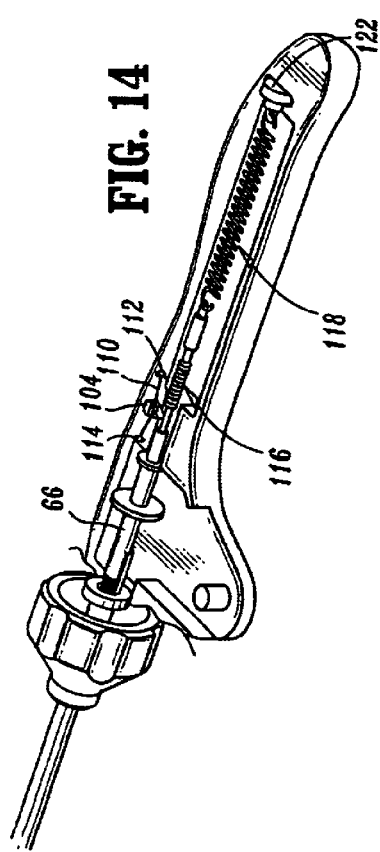
FIG. 14 is a perspective view of a cross-section of the clip applicator grip assembly.

Referring to FIG. 8, FIG. 9 and FIG. 12, the operation of the distal end 14 during application of a blood vessel clip can be seen in greater detail. FIG. 9 illustrates the distal end 14 immediately before the plunger 58 begins moving forward. FIG. 12 illustrates the distal end 14 after forward motion of the plunger 58 has ceased and before rearward motion of the plunger 58 has begun. As seen in FIG. 9, in a preferred embodiment a plurality of blood vessel clips 2 are located in the magazine passage 30. While it is within the scope of this invention to apply a single blood vessel clip 2 with the clip applicator 50, convenience and time considerations typically render it advantageous to provide a magazine passage 30 adapted to hold a plurality of blood vessel clips 2 and to insert a plurality of blood vessel clips 2 into the magazine passage 30 prior to insertion of the distal end 14 into the patient. One end of a clip stack stop spring 144 extends through the plunger slot 62, through the magazine passage 30, and into a spring recess 146. The other end of the clip stack stop spring 144 is attached to the magazine 28. A spring space 145 is located on the opposite side of the plunger slot 62 from the divider shim 68. The clip stack stop spring 144 extends into a space partially enclosed by the head 7 of the blood vessel clip 2 immediately behind the forward-most blood vessel clip 2 in the magazine passage 30. A tip 148 of the clip stack stop spring 144 rests in the spring recess 146 before the plunger 58 begins moving forward. Thus, the clip stack stop spring 144 prevents forward motion of the blood vessel clips 2 while the tip 148 rests in the spring recess 146.

As seen in FIG. 9, the forward-most blood vessel clip 2 is not restrained by the clip stack stop spring 144. Rather, it is located in the staging space 150 located between the passage having a constricted region 32 and the divider shim 68. The passage having a constricted region 32 is too narrow to allow the blood vessel clip 2 located in the staging space 150 to escape without being forced through.

When the plunger 58 advances, it begins pushing the blood vessel clip 2 in the staging area 150 toward the constricted region 32. Simultaneously, as the plunger 58 advances, the tip 148 of the clip stack stop spring 144 is preferably forced up through the plunger slot 62; the clip stack stop spring 144 bends upward into the spring space 145, as can be seen in FIG. 12. The clip stack stop spring 144 and plunger slot 62 are shaped such that the tip 148 is forced through the plunger slot 62 by the advancing plunger 58. The blood vessel clip 2 previously restrained by the clip stack stop spring 144 is thus freed to advance, at the same time that the plunger 58 is pushing the blood vessel clip 2 in the staging area 150 through the constricted region 32.

To apply the blood vessel clip 2 to a blood vessel 22, the distal end 14 is pushed over the blood vessel 22 such that the first pin 16 and the second pin 18 straddle the blood vessel 22. That is, the first pin 16 and the second pin 18 are located on opposite sides of the blood vessel 22, such that the blood vessel 22 lies between the first pin 16 and the second pin 18. The balls 20 serve to protect the blood vessel 22 from trauma while the distal end 14 is pushed over it. The surgeon then applies axial force to the clip applicator 50 in a direction somewhat transverse to the local centerline of the blood vessel 22. The balls 20 thus ride up over the walls of the blood vessel 22, eventually passing over its widest portion. The first pin 16 and the second pin 18 follow immediately behind the balls 20, and straddle the blood vessel 22. If the blood vessel 22 is larger than 5 mm in diameter, the first pin 16 and the second pin 18 pinch the blood vessel 22, but do not close it completely. The balls 20 allow the first pin 16 and the second pin 18 to ride up over the blood vessel 22 without damaging or injuring it.

Figure 5:
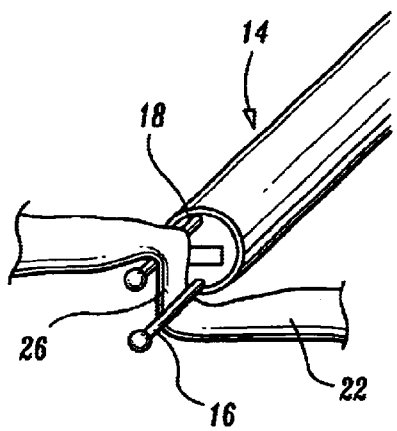
FIG. 5 is a perspective view of the distal end of a clip applicator after placement over a blood vessel and after rotation of the clip applicator.
Figure 10:
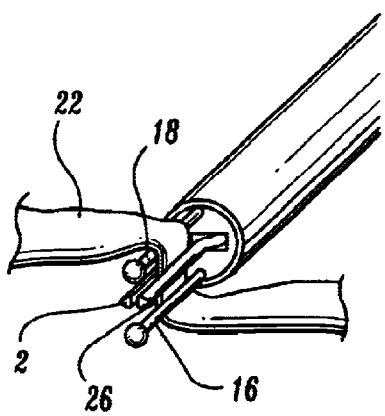
FIG. 10 is a perspective view of a blood vessel clip being applied to a blood vessel.
Figure 11:
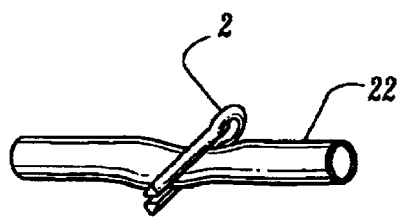
FIG. 11 is a perspective view of a blood vessel clip occluding a blood vessel.

After the first pin 16 and the second pin 18 are placed around the blood vessel 22, the distal end 14 is twisted substantially around the centerline of the magazine 28. Referring now to FIG. 5, force is applied to the blood vessel 22 where the first pin 16 and the second pin 18 contact it, tending to close the blood vessel 22 at those points, and between the first pin 16 and the second pin 18. The walls of the blood vessel 22 typically possess some degree of elasticity, so the torque exerted on the blood vessel 22 tends to stretch out the walls of the blood vessel 22. Referring to FIG. 4, assuming that the distal end 14 is rotated clockwise to apply torque to the blood vessel, the first pin 16 travels downward and to the right in a circular motion. Meanwhile, the second pin 18 travels upward and to the left in a circular motion as well. The first pin 16 and the second pin 18 thus tend to stretch the blood vessel 22 longitudinally while at the same time reducing the profile of the blood vessel 22 adjacent to the exit aperture 24. Referring to FIG. 5, it can be seen that the longitudinal and compressive forces exerted on the blood vessel 22 by the first pin 16 and the second pin 18 during rotation of the distal end 14 tend to flatten the portion 26 of the blood vessel 22 caught between the first pin 16 and the second pin 18. The distal end 14 may be rotated counterclockwise instead; the direction of rotation is irrelevant because the end result is the same.

After the distal end 14 has been rotated and the blood vessel 22 has been flattened, the blood vessel 22 is ready to accept a blood vessel clip 2. A blood vessel clip 2 can then be applied to the blood vessel 22 through the exit aperture 24 of the distal end 14. Referring to FIG. 6, the exit aperture 24 can be seen. The exit aperture 24 is an opening in the magazine 28 allowing for the ejection of blood vessel clips 2 from the magazine 28. The blood vessel clip or clips 2 are located in a magazine passage 30, which is a hollow area within the magazine 28. The constricted region 32 is formed by a first lobe 34 and a second lobe 36 spaced apart on opposite sides of the exit aperture 24, is located inside the magazine 28 adjacent to the exit aperture 24. The first lobe 34 and the second lobe 36 together preferably provide for a smooth and gradual transition to the narrowest point in the constricted region 32, and a smooth and gradual transition to the exit aperture 24 as well. A staging space 150 lies adjacent to the passage having a constricted region 32.

The blood vessel clip 2 nearest the exit aperture 24 is pushed toward the exit aperture 24 by a plunger 58, which will be described more fully below. The first leg 4 and the second leg 6 move into the passage having a constricted region 32, having little or no contact with the first lobe 34 or the second lobe 36. The blood vessel clip 2 is in the closed position as the first leg 4 and the second leg 6 pass into the constricted region 32, and both the first leg 4 and the second leg 6 together are preferably narrower than the constricted region 32. As the blood vessel clip 2 proceeds forward, the head 7 encounters the constricted region 32. The head 7 is wider than the constricted region 32. Thus, the first lobe 34 and the second lobe 36 exert a compressive force on the head 7 of the blood vessel clip 2 as the blood vessel clip 2 is forced into the constricted region 32. As the head 7 is compressed, the first leg 4 and the second leg 6 spread apart, and the blood vessel clip 2 moves toward the open position. As the blood vessel clip 2 moves forward, the first leg 4 and the second leg 6 extend further through the exit aperture 24. The first leg 4 and the second leg 6 begin to move over the blood vessel 22 such that the blood vessel 22 is between the first leg 4 and the second leg 6. The portion 26 of the blood vessel 22 that is compressed between the first pin 16 and the second pin 18 is located outside the exit aperture 24, at an angle to the exit aperture 24. Because the portion 26 of the blood vessel 22 is flattened compared to the normal state of the blood vessel 22 and presents a thinner aspect to the exit aperture 24, the blood vessel clip 2 can more easily be placed over the blood vessel 22, and can accommodate a larger blood vessel 22 than would be possible if the blood vessel 22 were not so flattened.

As the head 7 passes through the narrowest portion of the constricted region 32, the first leg 4 and the second leg 6 are spread apart to substantially the full extent of the open position. When the head 7 then begins to pass out of the constricted region 32 into the exit aperture, the force exerted by the constricted region 32 against the head 7 decreases, and the first leg 4 and the second leg 6 begin to close due to the spring-quality material composing the blood vessel clip 2. The head 7, and with it the blood vessel clip 2, is completely ejected from the exit aperture 24. Upon release, the first leg 4 and the second leg 6 close over the blood vessel 22. The blood vessel clip 2 exerts a substantially constant force on the blood vessel 22, due to the spring properties of the blood vessel clip 2 resulting from the use of a spring-quality material.

While the preferred embodiment has been described in terms of insertion of a surgical instrument and clips through a 5 mm cannula for occlusion of a blood vessel, it will be appreciated by one skilled in the art that the preferred embodiment may be scaled upward or downward while remaining capable of occluding blood vessels having diameters roughly equal to or less than the interior diameter of a cannula utilized for insertion of the instrument.

This preferred embodiment of the clip applicator 50 may be used with the preferred embodiment of blood vessel clip 2, or with the alternate embodiments of blood vessel clip 2 disclosed below.

ALTERNATE EMBODIMENT OF THE CLIP APPLICATOR

Figure 15:
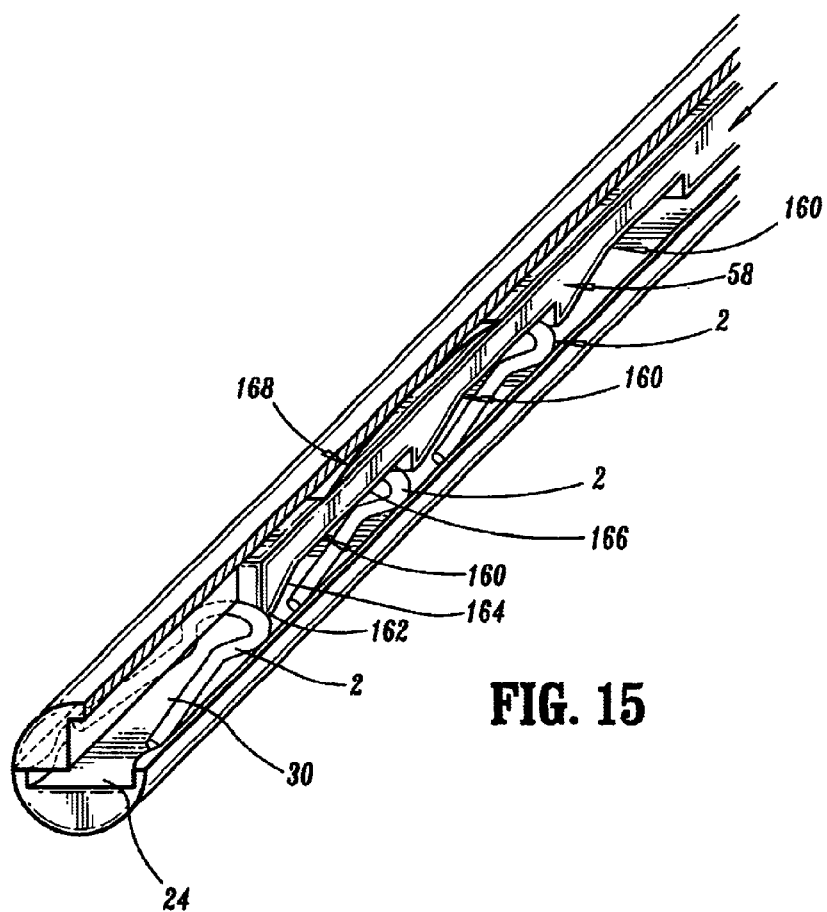
FIG. 15 is a cutaway view of an alternate embodiment of the clip applicator.

In an alternate embodiment of the clip applicator 50, a direct stroke approach is used to apply blood vessel clips 2. The alternate embodiment lacks several elements present in the preferred embodiment, allowing for simpler operation. Referring to FIG. 15, a perspective view of the alternate embodiment is shown. A plurality of blood vessel clips 2 are lined up in the magazine passage 30. Unlike the preferred embodiment, there is no staging space 150 or plunger space 70. The blood vessel clips 2 in the magazine passage 30 are lined up substantially on the same plane as the exit aperture 24, such that there is no need for a staging space 150 in which the blood vessel clip 2 moves between planes.

Figure 16:
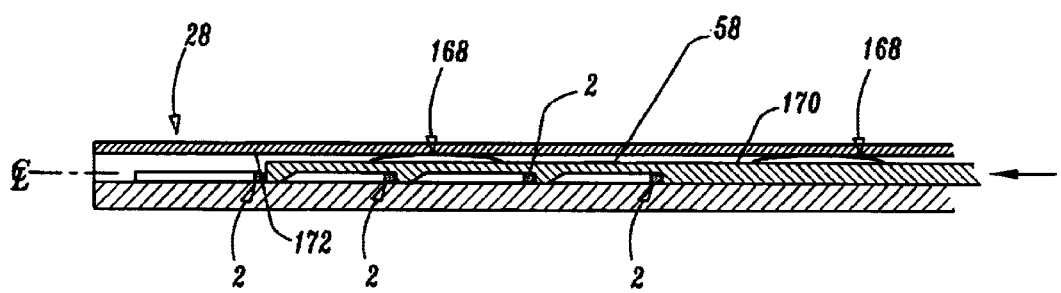
FIG. 16 is a cross-section view of an alternate embodiment of the clip applicator.

In the alternate embodiment, the plunger 58 is configured differently from the preferred embodiment. The plunger 58 possesses a plurality of stepwise indentations 160 facing the blood vessel clips 2, each stepwise indentation 160 having a tip 162, a ramp 164, and a ceiling 166. That is, the plunger 58 preferably includes a plurality of spaced protrusions, each protrusion having a tip 162 and a ramp 164. The plunger 58 is oriented relative to the blood vessel clips 2 such that each tip 162 is located immediately adjacent to each head 7 in the magazine passage 30, in the direction away from the exit aperture 24. In a particular stepwise indentation 160, the ramp 164 extends away from the tip 162 in a direction upward from the blood vessel clips 2 and away from the exit aperture 24. The ramp 164 then terminates in the ceiling 166, which is substantially parallel to the plane in which the blood vessel clips 2 lie. The ceiling 166 is spaced apart from the blood vessel clips 2 to substantially prevent contact between the ceiling 166 and the blood vessel clips 2. Referring to FIG. 16, one or more wire springs 168 are attached to an upper surface 170 of the plunger 58. The wire spring or springs 168 act against an inner wall 172 of the magazine 28, thereby forcing the plunger 58 downward toward the blood vessel clips 2.

Referring back to FIG. 15, to operate the alternate embodiment, the plunger 58 is pushed forward, in a manner such as disclosed with regard to the preferred embodiment. As the plunger 58 moves forward, the wire spring or springs 168 continue to bias the plunger 58 downward. Thus, each tip 162 of the plunger 58 remains in contact with the head 7 of one of the blood vessel clips 2, such that the blood vessel clips 2 are all pushed forward toward the exit aperture 24 by the tips 162 at the same time.

The frontmost blood vessel clip 2 is applied to the blood vessel 22 in the same manner as in the preferred embodiment. The frontmost blood vessel clip 2 is forced through the passage having a constricted region 32 by the frontmost tip 162 on the plunger 58. Just as in the preferred embodiment, the blood vessel clip 2 is clamped shut by the passage of the head through the constricted region 32.

Figure 15A:
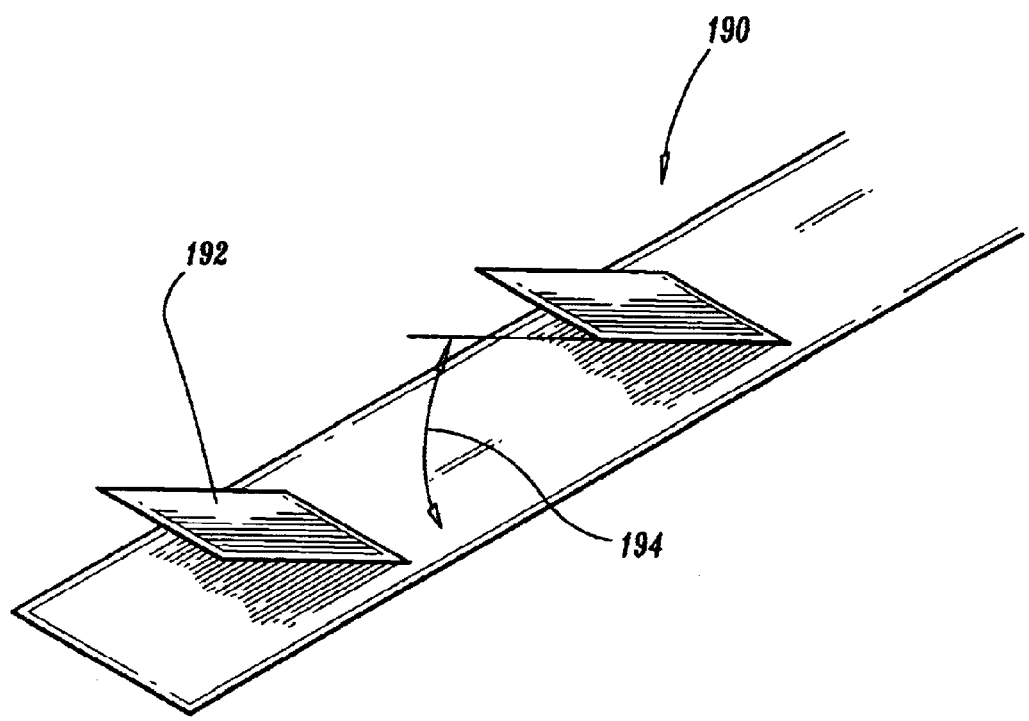
FIG. 15A is a perspective view of a lock mechanism for use with the alternate embodiment of the clip applicator.

After the plunger 58 has completed its stroke and the frontmost blood vessel clip 2 has been ejected through the exit aperture 24, the plunger 58 begins to retract. During this rearward motion of the plunger 58, the plurality of blood vessel clips 2 do not substantially move. Preferably, the blood vessel clips 2 are wide enough that friction between the blood vessel clips 2 and the magazine passage 30 prevents rearward motion of the blood vessel clips 2 during retraction of the plunger 58. Optionally, a positive locking mechanism can be utilized to prevent rearward motion of the blood vessel clips 2 during retraction of the plunger 58. It will be apparent to one skilled in the art that the positive locking mechanism can take many forms. For example, referring to FIG. 15A, a lock mechanism 190 may be inserted into the magazine passage 30, underneath the blood vessel clips 2. The lock mechanism 190 has a plurality of spring tabs 192 extending upward from and at an angle 194 to the lock mechanism 190. The angle 194 of each spring tab 192 opens toward the exit aperture 24. Each spring tab 192 is adapted to move downward toward the lock mechanism 190 as one of the heads 7 of one of the blood vessel clips 2 moves over it. When the plunger 58 retracts, any rearward motion of one of the blood vessel clips 2 will be arrested by one of the spring tabs 192, as the head 7 of the blood vessel clip 2 is caught in the angle 194 of the spring tab 192. In this way, the lock mechanism 190 provides a positive assurance that the blood vessel clips 2 will not move backward in the magazine passage 30. In an alternate embodiment, one or more spring tabs 192 may extend directly from a surface or surfaces of the magazine passage 30.

Figure 17:
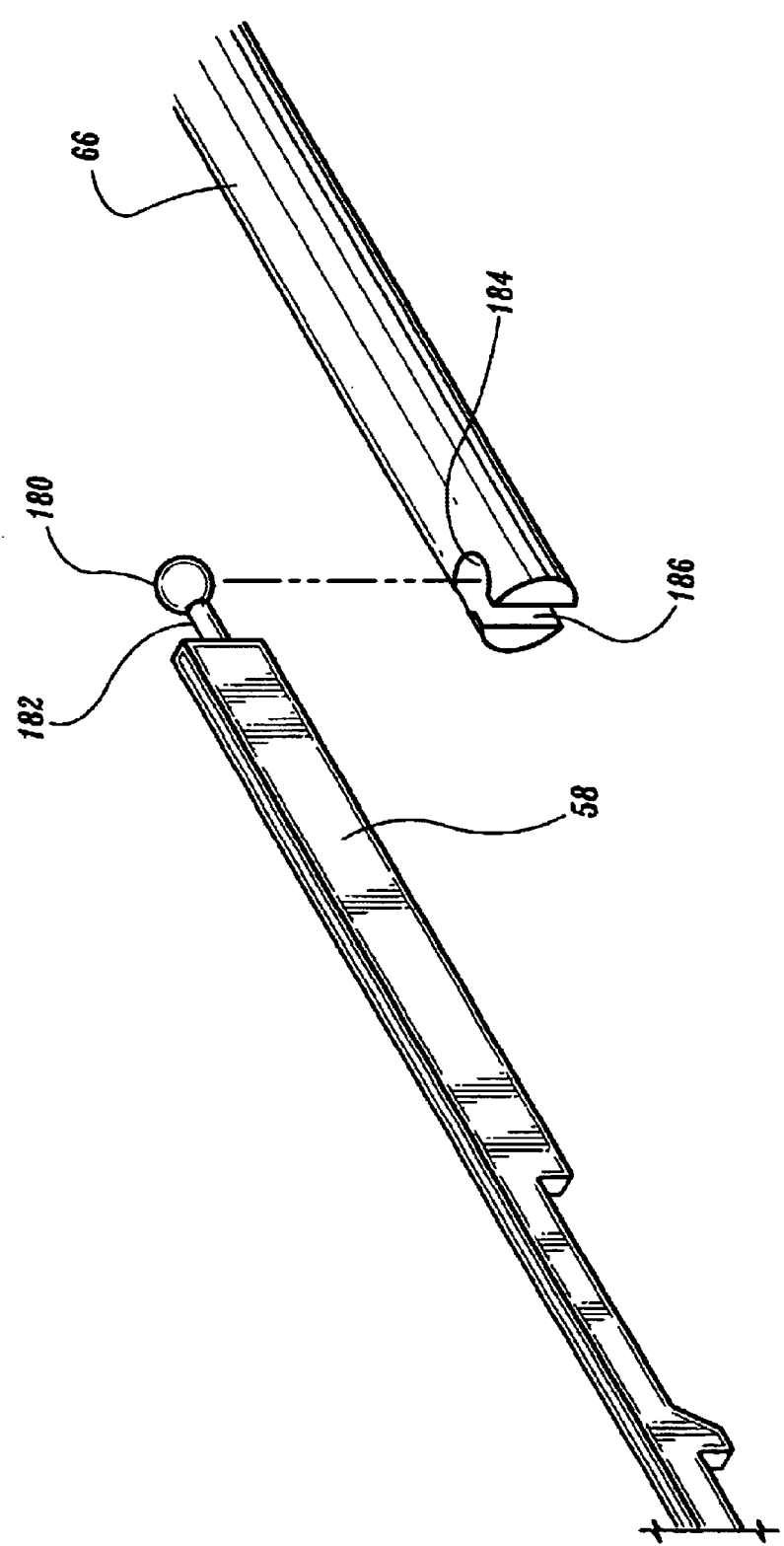
FIG. 17 is a perspective view of a detail of the alternate embodiment of the clip applicator.

Referring additionally to FIG. 17, the plunger 58 is directly attached to the ratchet rod 66 by an attachment ball 180 extending from a tip of the plunger 58 on an attachment ball extension 182. A receiving slot 184 extends substantially through an end of the ratchet rod 66 for receiving the attachment ball 180. The receiving slot 184 is thus substantially cylindrical in shape. A substantially vertical slot opening 186 is located at a tip of the ratchet rod 66, and allows for the attachment ball extension 182 to fit therein. The receiving slot 184 allows the attachment ball 180, and thus the plunger 58, to move up and down. As the plunger 58 retracts, the plunger 58 moves upward, allowing it to more easily pass backward over the blood vessel clips 2.

The plunger 58 moves backward substantially unimpeded until each ramp 164 encounters the surface of one of the heads 7 that faces toward the exit aperture 24. As the plunger 58 continues to move rearward, it begins to ride upward over the blood vessel clips 2 as each ramp 164 moves over each head 7. As the plunger 58 continues its rearward motion, each ramp 164 passes over each head 7, and the wire spring or springs 168 push the plunger 58 back downward again such that the surface of each head 7 facing away from the exit aperture 24 is once again adjacent to one of the tips 162. The clip applicator 50 is thus ready to apply another blood vessel clip 2. This alternate embodiment of the clip applicator 50 may be used with the preferred embodiment of blood vessel clip 2, or with the alternate embodiments of the blood vessel clip 2 disclosed below.

ALTERNATE EMBODIMENTS OF THE BLOOD VESSEL CLIP

Alternate embodiments of the blood vessel clip 2 are contemplated for use with the clip applicator 50. Each of the alternate embodiments of the blood vessel clip 2 are malleable, instead of spring-quality, in contrast to the preferred embodiment. The alternate embodiments of the blood vessel clip 2 are in a substantially annealed condition, and preferably not pretensioned or prestressed within the clip applicator 50.

Figure 18:
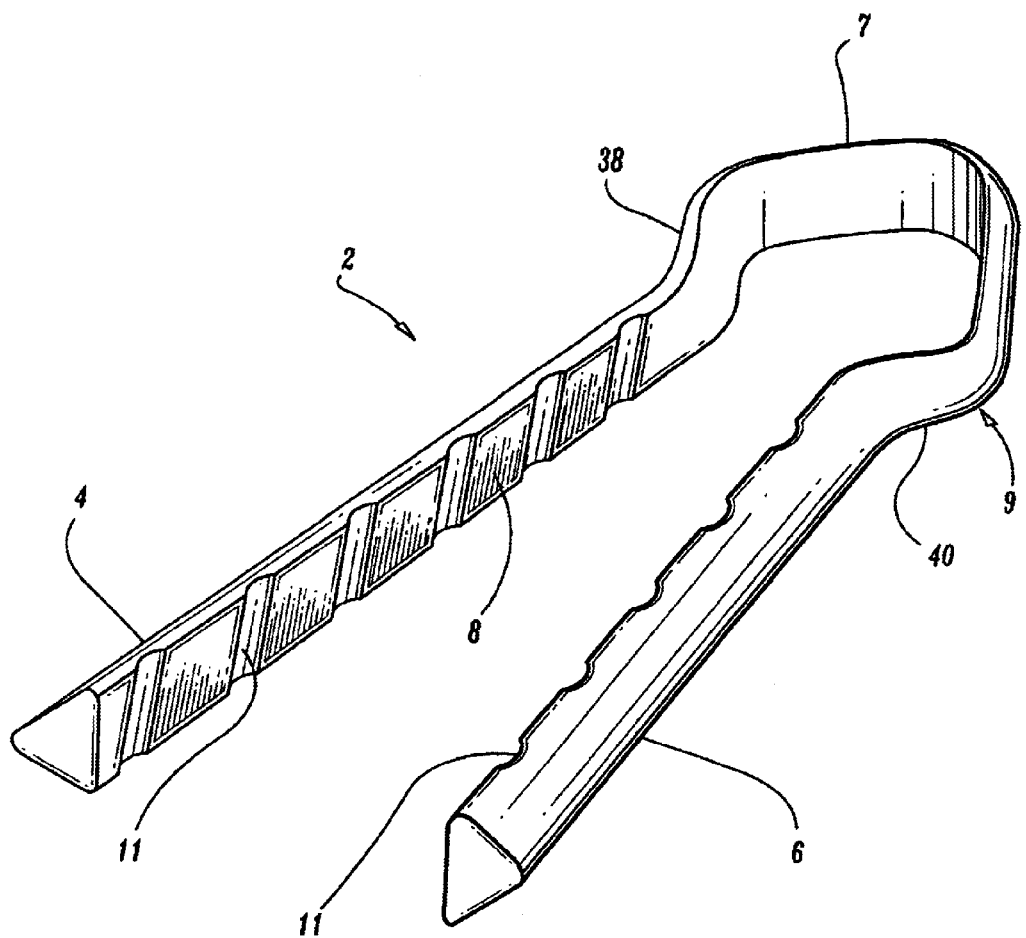
FIG. 18 is a perspective view of a first alternate embodiment of a blood vessel clip.

Referring to FIG. 18, in a first alternate embodiment, the head 7 preferably bulges outward such that the head 7 takes the shape of the outline of a diamond missing one corner. That is, the head 7 has a point, extends substantially linearly outward to a maximum width, then narrows once again, also substantially linearly, until the head 7 connects to the first leg 4 and the second leg 6. The first leg 4, the second leg 6 and the head 7 are preferably arranged such that the blood vessel clip 2 lies substantially in one plane and is substantially bilaterally symmetrical. In a preferred embodiment, the first leg 4 and the second leg 6 are positioned at an angle to one another, such that the first leg 4 and second leg 6 form a substantial "V" shape relative to one another. The first leg 4, the second leg 6 and the head 7 preferably have a substantially triangular cross-section, as seen in FIG. 18. The first leg 4 has a first leg inner surface 8 that is substantially planar, and the second leg 6 has a second leg inner surface 10 that is also substantially planar. The first leg inner surface 8 faces toward the second leg inner surface 10 across the space separating the first leg 4 and the second leg 6. A plurality of grooves 11 are located on the first leg inner surface 8 and the second leg inner surface 10. Preferably, the grooves 11 are diagonally opposed, and serve to grip a blood vessel once the blood vessel clip 2 has been placed onto it and closed. While the same clip applicator 50 may be used to apply the first alternate embodiment of the blood vessel clip 2 to the blood vessel 22, the mechanism of closure of the blood vessel clip 2 is different. As the plunger 58 pushes the first alternate embodiment of the blood vessel clip 2 forward, the first leg 4 and the second leg 6 of the blood vessel clip 2 are the first parts of the blood vessel clip 2 to encounter the constricted region 32. The first leg 4 encounters the first lobe 34 and the second leg 6 encounters the second lobe 36 as the blood vessel clip 2 is pushed toward the exit aperture 24. As the blood vessel clip 2 proceeds into the constricted region 32, the first leg 4 and the second leg 6 are compressed elastically toward one another by the first lobe 34 and the second lobe 36. However, the constricted region 32 is not so pronounced as to cause permanent closure of the space between the first leg 4 and the second leg 6. Because the first leg 4 and second leg 6 are preferably angled relative to one another, as seen in FIG. 1, it can be seen that the greatest deflection of the first leg 4 and the second leg 6, while the first leg 4 and the second leg 6 are traveling through the constricted region 32, occurs when the first leg 4 and the second leg 6 initially enter the constricted region 32. The first leg 4 and the second leg 6 are closer together nearer the head 7, so the constricted region 32 applies less force to the first leg 4 and the second leg 6 by the time the head 7 has almost entered the constricted region 32.

Referring back to FIG. 6, as the blood vessel clip 2 proceeds into the constricted region 32, the first leg 4 and the second leg 6 begin to extend through the exit aperture 24. As the blood vessel clip 2 proceeds forward, the first leg 4 and the second leg 6 begin to move over the blood vessel 22 such that the blood vessel 22 is between the first leg 4 and the second leg 6. Due to the location of the first pin 16 and the second pin 18 relative to the exit aperture 24, the portion 26 of the blood vessel 22 is flattened between the first pin 16 and the second pin 18 in a plane substantially perpendicular to the widest dimension of the exit aperture 24. Thus, the first leg 4 and the second leg 6 move around opposite sides of the blood vessel 22. Because the portion 26 of the blood vessel 22 is flattened compared to the normal state of the blood vessel 22 and presents a thinner aspect to the exit aperture 24, the blood vessel clip 2 can accommodate a larger blood vessel 22 than would be possible if the blood vessel 22 were not so flattened.

As the blood vessel clip 2 continues to proceed forward, the head 7 begins to encounter the constricted region 32, because the head 7 is wider than the constricted region 32. The constricted region 32 is not so narrow, however, to close the first leg 4 and the second leg 6 before the blood vessel 22 is properly positioned between the first leg 4 and the second leg 6. For the head 7 to pass through the constricted region 32, the head 7 must deform permanently. This deformation of the head 7 closes the blood vessel clip 2 over the blood vessel 22. Sequentially, as the blood vessel clip 2 is pushed through the constricted region 32, the head 7 eventually encounters the first lobe 34 and the second lobe 36. Referring to FIG. 18 and FIG. 6, due to the preferred shape of the head 7, a first front area 38 initially encounters the first lobe 34, and a second front area 40 initially encounters the second lobe 36. As the blood vessel clip 2 proceeds toward the exit aperture 24, the first lobe 34 exerts a force against the first front area 38, and the second lobe 36 exerts a force against the second front area 40. The first front area 38 and the second front area 40 thus begin to deform as they pass into the constricted region 32. As the head 7 deforms, this deformation causes the first leg 4 and the second leg 6 to begin closing together relative to one another. As the blood vessel clip 2 continues through the constricted region 32, a wide portion 9 of the head 7 eventually passes into the constricted region 32. Because the wide portion 9 of the head 7 is wider than the constricted region 32, the head 7 has to deform in order to pass through the constricted region 32. This deformation permanently alters the shape of the head, crushing the wide portion 9 of the head 7 such that it is essentially as wide as the narrowest point in the constricted region 32. This crushing of the wide portion 9 of the head 7 also forces the first leg 4 and the second leg 6 together, such that they clamp tightly over the blood vessel 22 and occlude it. The deformation in the blood vessel clip 2 after the head 7 passes through the constricted region 32 is shown in FIG. 7. The blood vessel clip 2, attached to the blood vessel 22, is then completely ejected through the exit aperture 24.

Figure 19:
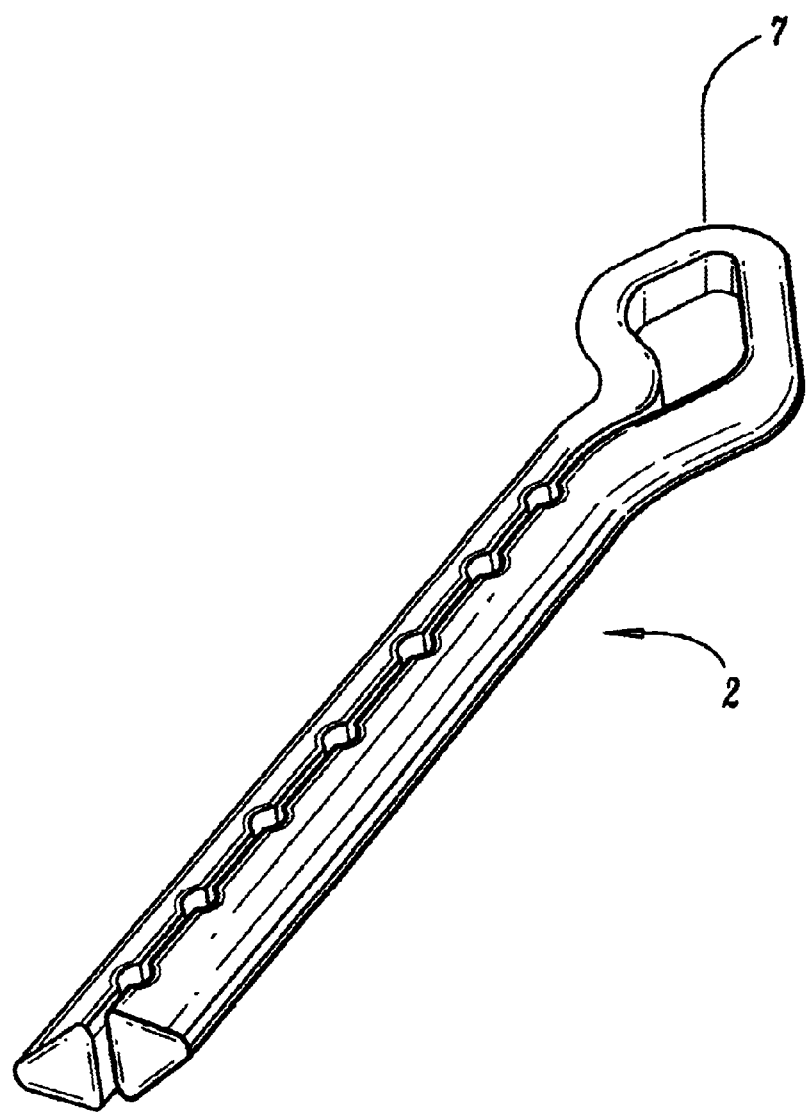
FIG. 19 is a perspective view of a second alternate embodiment of a blood vessel clip.

In a second alternate embodiment, if it is desired to prevent the blood vessel 22 from being positioned within or migrating into the head 7, one leg may be offset from the other to block the entrance of the blood vessel 22 into the head 7, as shown in FIG. 19. By offsetting the first leg 4 from the second leg 6, the head 7 takes on a small amount of asymmetry without affecting the operation of the blood vessel clip 2. As can be seen in FIG. 19, where the first leg 4 meets the head 7, it is immediately adjacent to the second leg 6, rather than spaced apart from it. Further, while the second leg 6 is shaped as in the first alternate embodiment, the first leg 4 is shaped differently. The first leg 4 is formed such that the end of the first leg 4 attached to the head 7 at least partially crosses the longitudinal centerline of the blood vessel clip 2 and abuts the second leg 6. By pinching the first leg 4 and the second leg 6 close together immediately before the head 7, the likelihood that the blood vessel 22 will be placed into or will move into the head 7 is reduced. In this second alternate embodiment, the first leg 4 and the second leg 6 may be offset from a longitudinal centerline of the blood vessel clip 2. It will be apparent to one of ordinary skill in the art that the second leg 6 could instead be shaped differently from the first alternate embodiment.

Figure 20:
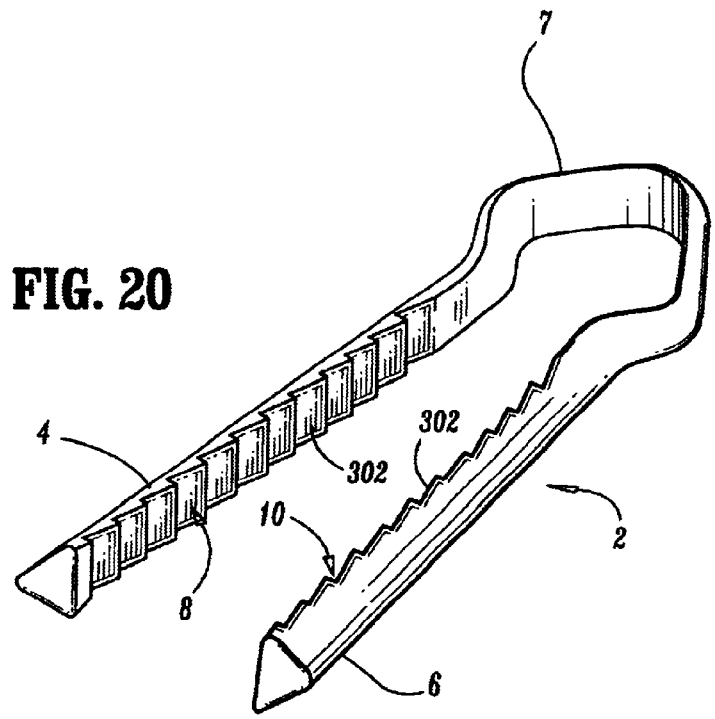
FIG. 20 is a perspective view of a third alternate embodiment of a blood vessel clip.

Referring to FIG. 20, in a third alternate embodiment, a third alternate blood vessel clip 300 is shown, the first leg 4 and the second leg 6 spaced apart from one another and connected by the head 7. The head 7 preferably bulges outward such that the head 7 takes the shape of the outline of a diamond missing one corner. That is, the head 7 has a point, extends substantially linearly outward to a maximum width, then narrows once again, also substantially linearly, until the head 7 connects to the first leg 4 and the second leg 6. The first leg 4 and the second leg 6 are at an angle to one another, such that the first leg 4 and the second leg 6 form a substantial "V" shape relative to one another. The blood vessel clip 300 comprises a wire having a substantially triangular cross section, bent into the shape of the blood vessel clip 300. The first leg inner surface 8 and the second leg inner surface 10 each have a plurality of sawteeth 302 formed into them. These sawteeth 302 are positioned in a steplike manner on the first leg inner surface 8 and the second leg inner surface 10. The sawteeth 302 are angled relative to the first leg 4 and the second leg 6, the direction of these angles opening toward the head 7 of the blood vessel clip 2. The sawteeth 302 are all angled in substantially the same direction at substantially the same angle, referred to as a one-way arrangement. The effect of the sawteeth 302 is thus to prevent motion of the blood vessel clip 300 in a direction toward the free ends of the first leg 4 and the second leg 6.

Figure 21:
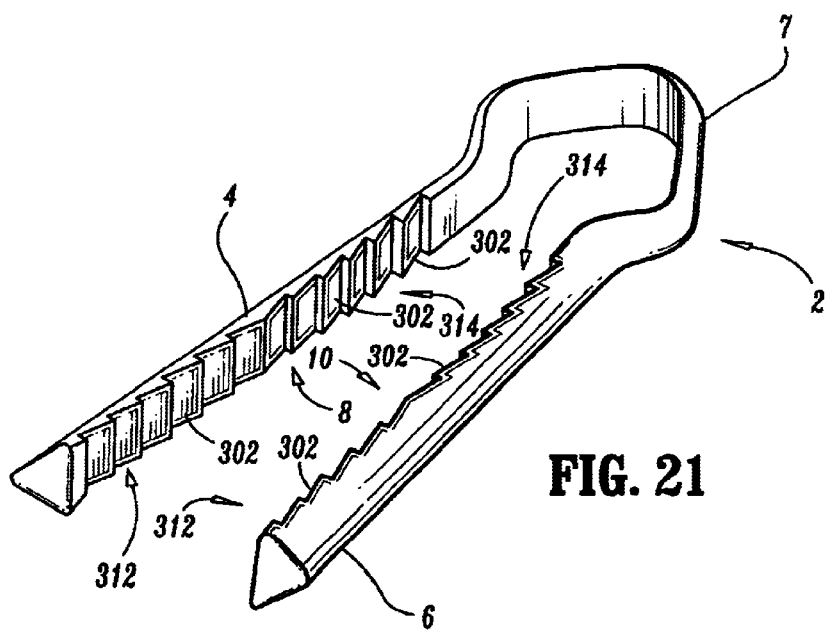
FIG. 21 is a perspective view of a fourth alternate embodiment of a blood vessel clip.

Referring to FIG. 21, in a fourth alternate embodiment, a second alternate blood vessel clip 310 is shown. The fourth alternate blood vessel clip 310 varies from the first alternate blood vessel clip 300 in one respect: the orientation of the sawteeth 302. On the fourth alternate blood vessel clip 310, the sawteeth 302 are oriented in two directions. On a first section 312 of both the first leg inner surface 8 and the second leg inner surface 10 located further from the head 7, the sawteeth 302 are angled in the same manner as the first alternate blood vessel clip 300. The angle of each sawtooth 302 in the first section 312 opens toward the head 7 to resist motion of the second alternate blood vessel clip 310 in a direction toward the head 7. On a second section 314 of both the first leg inner surface 8 and the second leg inner surface 10 located closer to the head 7, the sawteeth 302 are oriented in the opposite direction from the sawteeth 302 in the first section 312. The angle of each sawtooth 302 in the second section 314 opens away from the head, to resist motion of the second alternate blood vessel clip 310 in a direction away from the head 7. The use of sawteeth facing opposite directions and resisting motion in two directions is referred to as a two-way sawtooth arrangement.

Figure 22:
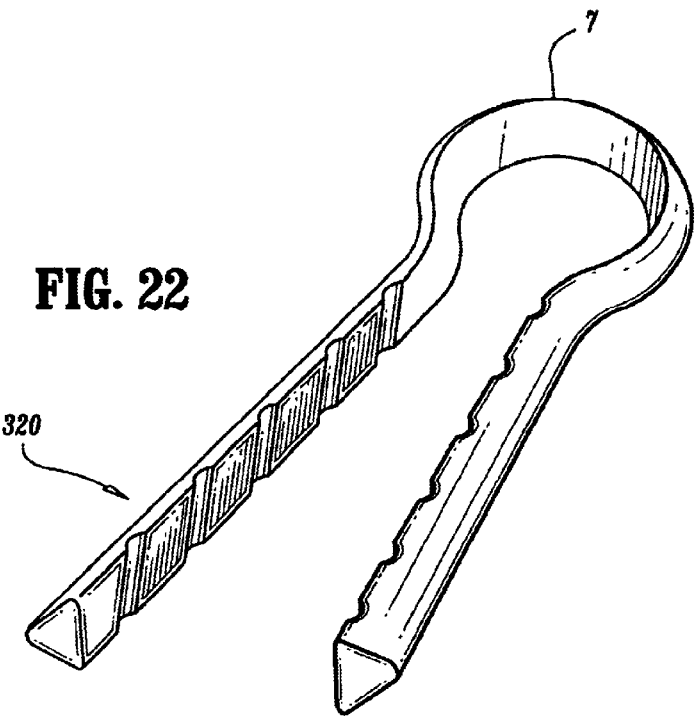
FIG. 22 is a perspective view of a fifth alternate embodiment of a blood vessel clip.

Referring to FIG. 22, in a fifth alternate embodiment, a fifth alternate blood vessel clip 320 is shown. The fifth alternate blood vessel clip 320 is similar to the blood vessel clip 2, but differs from the blood vessel clip 2 in the configuration of the head 7. The head 7 of the fifth alternate blood vessel clip 320 is substantially circular, rather than diamond-shaped. The head 7 of the fifth alternate blood vessel clip 320 is adapted to be deformed when it passes through the constricted region 32, just as the head 7 of the blood vessel clip 2 is deformed when forced through the constricted region 32.

Figure 23:
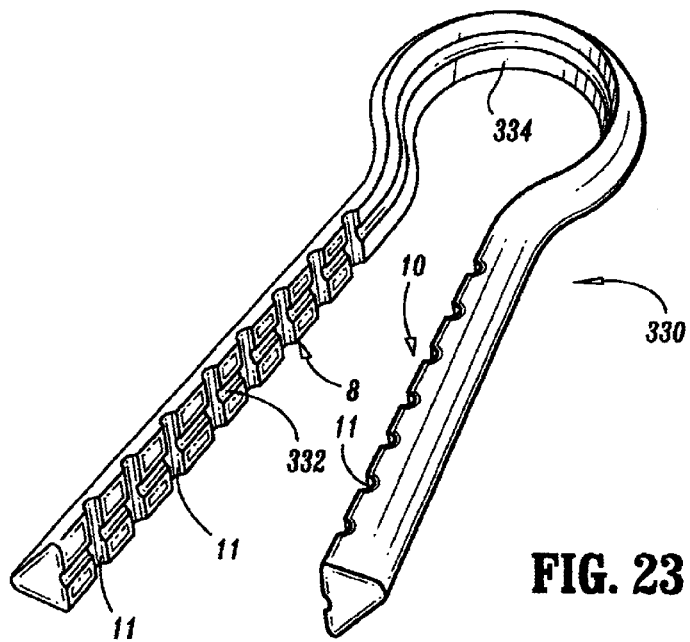
FIG. 23 is a perspective view of a sixth alternate embodiment of a blood vessel clip.

Referring to FIG. 23, in a sixth alternate embodiment, a sixth alternate blood vessel clip 330 is shown. The sixth alternate blood vessel clip 330 is similar to the fifth alternate blood vessel clip 320, but differs in the configuration of the grooves 11. In the sixth alternate blood vessel clip 330, the head 7 is substantially circular. The grooves 11 are substantially vertical. Further, a keyway 332 extends from the first leg inner surface 8, around a head inner surface 334, and down the second leg inner surface 10. The keyway 332 substantially lies in a plane bisecting the fourth alternate blood vessel clip 330. The keyway 332 acts to resist motion of the sixth alternate blood vessel clip 330 in a direction substantially perpendicular to the plane in which the sixth alternate blood vessel clip 330 substantially lies.

Figure 24:
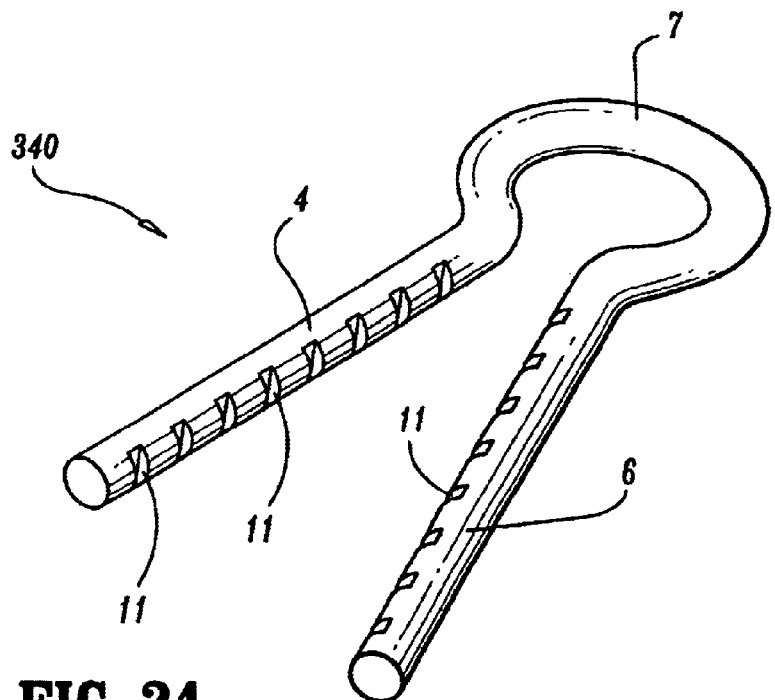
FIG. 24 is a perspective view of a seventh alternate embodiment of a blood vessel clip.

Referring to FIG. 24, in a seventh alternate embodiment, a seventh alternate blood vessel clip 340 is shown. In the seventh alternate blood vessel clip 340, the first leg 4, the second leg 6 and the head 7 have a substantially circular cross section. The seventh alternate blood vessel clip 340 is preferably formed from a wire having a substantially circular cross-section. Grooves 11 are cut into the first leg inner surface 8 and the second leg inner surface 10, and may be substantially vertical, as shown in FIG. 24, or arranged diagonally.

Figure 25:
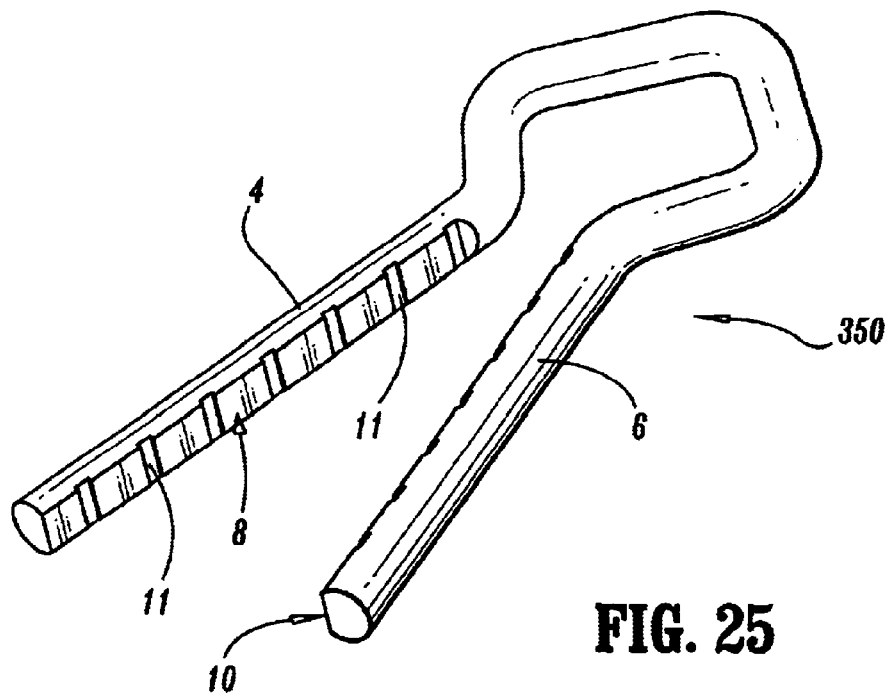
FIG. 25 is a perspective view of a eighth alternate embodiment of a blood vessel clip.

Referring to FIG. 25, in an eighth alternate embodiment, an eighth alternate blood vessel clip 350 is shown. The eighth alternate blood vessel clip 350 is similar to the seventh alternate blood vessel clip 340. However, the cross section of the first leg 4 and the second leg 6 is not entirely circular. Rather, it possesses a flat portion along a chord of the substantially circular cross section, such that the eighth alternate blood vessel clip 350 has a first leg inner surface 8 and a second leg inner surface 10 that are substantially planar. The grooves 11 located on the first leg inner surface 8 and the second leg inner surface 10 are may be substantially vertical, as shown in FIG. 25, or arranged diagonally.

Figure 26:
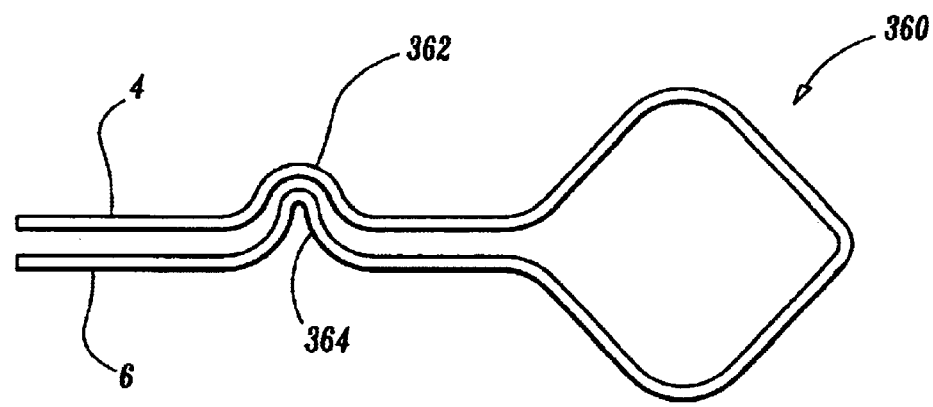
FIG. 26 is a top view of a ninth alternate embodiment of a blood vessel clip.

It is also within the scope of this invention to provide mating features in a blood vessel clip 2, to promote occlusion of the blood vessel 22 after application. Referring to FIG. 26, a ninth alternate embodiment 360 is shown, which is another variation of the annealed clip. In the ninth alternate embodiment 360, the first leg 4 has a first mating bend 362, and the second leg 6 has a second mating bend 364. The first mating bend 362 and the second mating bend 364 both extend laterally, in substantially the same direction and plane. The second mating bend 364 is adapted to fit substantially into an inner surface of the first mating bend 362, such that the first mating bend 362 and the second mating bend 364 can together apply a concentrated force to the blood vessel 22 caught between them. It will be obvious to one skilled in the art that the first mating bend 362 and the second mating bend 364 can be provided in the preferred blood vessel clip 2 as well, where the first mating bend 362 and the second mating bend 364 are held together by the force exerted by the spring-quality material of the blood vessel clip 2 as the blood vessel clip 2 biases toward a closed position. It will also be obvious to one skilled in the art that the first mating bend 362 and second mating bend 364 may be oriented in the opposite direction, such that the first mating bend 362 is adapted to fit substantially into an inner surface of the second mating bend 364.

Figure 27:
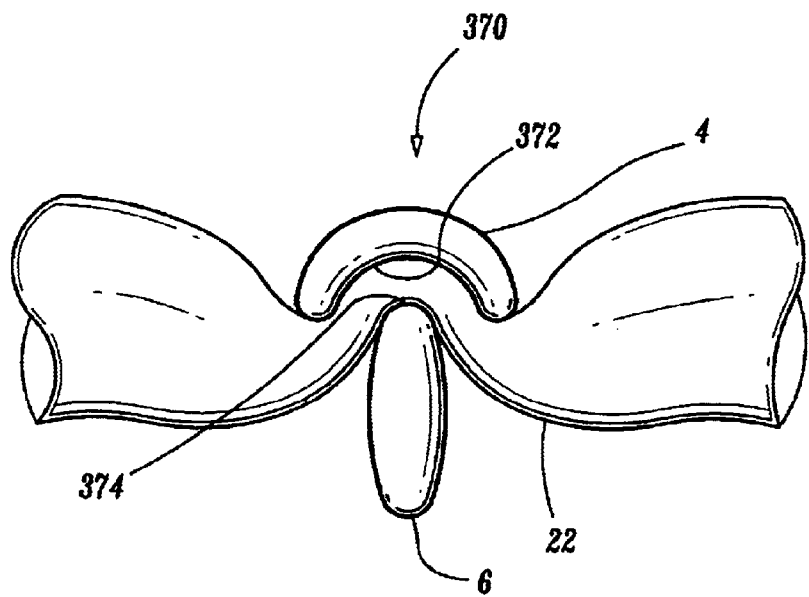
FIG. 27 is a cross-section view of the legs of a tenth alternate embodiment of a blood vessel clip.

Referring to FIG. 27, in a tenth alternate embodiment 370, a different kind of mating configuration is seen. In the tenth alternate embodiment 370, the first leg 4 has a first leg indentation 372 extending substantially along its length. The first leg indentation 372 is smooth and atraumatic, and preferably takes the shape of a semicircular arc. The second leg 6 has a second leg mating surface 374 adapted to fit into the first leg indentation 372. The second leg mating surface 374 is also smooth and atraumatic. During closure of the tenth alternate embodiment 370, the second leg 6 forces the blood vessel 22 up into the first leg indentation 372, promoting its occlusion. As in the ninth alternate embodiment 360, it will be obvious to one skilled in the art that the first leg indentation 372 and the second leg mating surface 374 can be provided in the preferred blood vessel clip 2 as well, where the second leg mating surface 374 is pushed toward the first leg indentation 372 by the force exerted by the spring-quality material of the blood vessel clip 2 as the blood vessel clip 2 biases toward a closed position. It will also be obvious to one skilled in the art that the first leg indentation 372 and the second leg mating surface 374 may be switched to opposite legs of the tenth alternate embodiment 370 without changing its functionality.

A preferred blood vessel clip and applicator, and alternate blood vessel clips and applicators, and many of their attendant advantages have thus been disclosed. It will be apparent, however, that various changes may be made in the materials and components without departing from the spirit and scope of the invention, the materials and components hereinbefore described being merely preferred or exemplary embodiments thereof. Therefore, the invention is not to be restricted or limited except in accordance with the following claims and their legal equivalents.

What is claimed is:

1. An apparatus for placing over a blood vessel a blood vessel clip comprising spring-quality material and having a head, comprising:
   an applicator barrel having a distal end;
   an exit aperture in said distal end of said applicator barrel;
   a constricted region narrower than the head of the blood vessel clip, said constricted region spaced apart from said exit aperture and having a narrowest point narrower than said exit aperture; and
   means for impelling the blood vessel clip through said constricted region, whereby compression of the head as it enters said constricted region forces the blood vessel clip open.

2. The apparatus of claim 1, wherein said impelling means comprises a plunger operably connected to a grip assembly.

3. The apparatus of claim 1, further comprising:
   a grip assembly having a handle and a trigger, said grip assembly attached to said applicator barrel;
   a magazine connected to said applicator barrel, said magazine having a plunger space and a magazine passage separated by a divider shim, said magazine passage adapted to hold one or more blood vessel clips; and
   a plunger extending into said plunger space, said plunger operably connected to said grip assembly and adapted to impel the blood vessel clip through said constricted region and said exit aperture.

4. The apparatus of claim 3, further comprising a first pin extending distally from said magazine on one side of said exit aperture and a second pin extending distally from said magazine on substantially the other side of said exit aperture.

5. The apparatus of claim 3, wherein said first pin and said second pin are substantially parallel to the axial centerline of said magazine.

6. The apparatus of claim 3, further comprising a protective ball attached to the distal end of both said first pin and said second pin.

7. The apparatus of claim 3, further comprising a rotating knob attached to said applicator barrel substantially coaxially with said applicator barrel.

8. The apparatus of claim 3, further comprising a staging space between said constricted region on one end and said plunger space and said magazine passage on the other.

9. The apparatus of claim 3, further comprising:
   a ratchet rod operably connected to said plunger, said ratchet rod extending into said handle;
   a rear chamber in said handle into which said ratchet rod extends;
   a rotating wheel attached to said handle within said rear chamber, said rotating wheel having an axis of rotation substantially coaxial with the axial centerline of said ratchet rod; and
   a return spring connecting the proximal end of said ratchet rod to said rotating wheel.

10. An apparatus for flattening a blood vessel, said apparatus comprising:
    an applicator barrel having a distal end;
    an exit aperture in said distal end of said applicator barrel;
    a first pin extending distally from said applicator barrel on one side of said exit aperture; and
    a second pin extending distally from said applicator barrel on substantially the opposite side of said exit aperture from said first pin.

11. The apparatus of claim 10, wherein said first pin and said second pin are substantially parallel to a centerline of said applicator barrel.

12. The apparatus of claim 10, further comprising a protective ball attached to the distal end of both said first pin and said second pin.

13. The apparatus of claim 10, further comprising a rotating knob attached to said applicator barrel substantially coaxially with said applicator barrel.

14. The apparatus of claim 13, said rotating knob having an index cavity with an opening, inside which an indexing spring biases an indexing ball toward said opening, said indexing ball adapted to fit against an index mark located in said handle when said opening is positioned adjacent said indexing mark.

15. An apparatus for applying to a blood vessel a blood vessel clip having a wide portion, comprising:
    a grip assembly having a handle and a trigger;
    an applicator barrel attached to said grip assembly;
    a magazine connected to said applicator barrel, said magazine having a plunger space and a magazine passage separated by a divider shim, said magazine passage adapted to hold one or more blood vessel clips;
    an exit aperture in said magazine through which the blood vessel clip is ejected;
    a constricted region adjacent to said exit aperture, said constricted region narrower than the wide portion of the head of the blood vessel clips;
    a plunger extending into said plunger space, said plunger operably connected to said grip assembly and adapted to serially impel said blood vessel clips through said constricted region and exit aperture;

a first pin extending distally from said magazine on one side of said exit aperture, substantially parallel to a centerline of said magazine;

a second pin extending distally from said magazine on substantially the other side of said exit aperture from said first pin, substantially parallel to a centerline of said magazine;

a protective ball attached to the distal end of both said first pin and said second pin;

a rotating knob attached to said applicator barrel substantially coaxially;

a ratchet rod extending into said handle and operably connected to said plunger, said ratchet rod;

a rear chamber in said handle into which said ratchet rod extends;

a rotating wheel attached to said handle within said rear chamber, said rotating wheel having an axis of rotation substantially coaxial with said ratchet rod; and a return spring connecting the proximal end of said ratchet rod to said rotating wheel.

16. An apparatus for crimping a substantially annealed blood vessel clip having a head, comprising:

an applicator barrel having a distal end;

an exit aperture in said distal end of said applicator barrel;

a constricted region narrower than the head of the blood vessel clip, said constricted region adjacent to said exit aperture; and means for impelling the blood vessel clip through said constricted region, whereby the head is deformed to clamp the blood vessel clip shut.

17. The apparatus of claim 16, where said means for impelling is a plunger operably connected to a grip assembly.

* * * * *